US011756667B2

(12) United States Patent
Lou et al.

(10) Patent No.: US 11,756,667 B2
(45) Date of Patent: Sep. 12, 2023

(54) DECISION SUPPORT SYSTEM FOR MEDICAL THERAPY PLANNING

(71) Applicant: Siemens Healthcare GmbH, Erlangen (DE)

(72) Inventors: Bin Lou, Princeton, NJ (US); Ali Kamen, Skillman, NJ (US)

(73) Assignee: Siemens Healthcare GmbH, Erlangen (DE)

(*) Notice: Subject to any disclaimer, the term of this patent is extended or adjusted under 35 U.S.C. 154(b) by 1251 days.

(21) Appl. No.: 16/270,743

(22) Filed: Feb. 8, 2019

(65) Prior Publication Data

US 2019/0371450 A1 Dec. 5, 2019

Related U.S. Application Data

(60) Provisional application No. 62/745,712, filed on Oct. 15, 2018, provisional application No. 62/677,716, filed on May 30, 2018.

(51) Int. Cl.
*G16H 20/40* (2018.01)
*G16H 50/30* (2018.01)
(Continued)

(52) U.S. Cl.
CPC .......... *G16H 20/40* (2018.01); *A61B 5/7267* (2013.01); *A61N 5/103* (2013.01); *G06N 3/04* (2013.01);
(Continued)

(58) Field of Classification Search
CPC ........ G16H 20/40; G16H 50/30; G16H 50/20; A61B 5/7267; A61B 6/032; A61N 5/103; G06N 3/04; G06T 7/0012; G06T 2207/10081; G06T 2207/20081; G06T 2207/20084

See application file for complete search history.

(56) References Cited

U.S. PATENT DOCUMENTS 10,395,141 B2  8/2019  Bobovich et al.
11,132,797 B2  9/2021  Mao et al.
(Continued)

FOREIGN PATENT DOCUMENTS

CN     107451620 A    12/2017
CN     108053025 A    5/2018
WO  WO2018048575 A1   3/2018

OTHER PUBLICATIONS

Cunliffe, Alexandra, et al. "Lung texture in serial thoracic computed tomography scans: correlation of radiomics-based features with radiation therapy dose and radiation pneumonitis development." International Journal of Radiation Oncology* Biology* Physics 91.5 (2015): 1048-1056.
(Continued)

*Primary Examiner* — David P Porta
*Assistant Examiner* — Fani Polyzos Boosalis

(57) ABSTRACT

For decision support in a medical therapy, machine learning provides a machine-learned generator for generating a prediction of outcome for therapy personalized to a patient. Deep learning may result in features more predictive of outcome than handcrafted features. More comprehensive learning may be provided by using multi-task learning where one of the tasks (e.g., segmentation, non-image data, and/or feature extraction) is unsupervised and/or draws on a greater number of training samples than available for outcome prediction alone.

20 Claims, 7 Drawing Sheets

(51) Int. Cl.

| | | |
|---|---|---|
| *G16H 50/20* | (2018.01) | |
| *A61B 5/00* | (2006.01) | |
| *G06T 7/00* | (2017.01) | |
| *A61N 5/10* | (2006.01) | |
| *G06N 3/04* | (2023.01) | |
| *A61B 6/03* | (2006.01) | |

(52) U.S. Cl.
CPC .......... *G06T 7/0012* (2013.01); *G16H 50/20* (2018.01); *G16H 50/30* (2018.01); *A61B 6/032* (2013.01); *G06T 2207/10081* (2013.01); *G06T 2207/20081* (2013.01); *G06T 2207/20084* (2013.01)

(56) References Cited

U.S. PATENT DOCUMENTS

2004/0116804 A1  6/2004  Mostafavi
2017/0357844 A1  12/2017  Comaniciu et al.
2018/0144209 A1  5/2018  Kim et al.

OTHER PUBLICATIONS

David J. Brenner, Ph.D., D.Sc. "Point: The linear-quadratic model is an appropriate methodology for determining iso-effective doses at large doses per fraction" Oct. 2008 ; 18(4): 234-239.

Extended European Search Report (EESR) dated Sep. 10, 2019 in corresponding European Patent Application No. 19177161.7.

Aerts, Hugo JWL, et al. "Decoding tumour phenotype by noninvasive imaging using a quantitative radiomics approach." Nature communications 5 (2014): 1-8.

Gillies, Robert J., et al. "Radiomics: images are more than pictures, they are data." Radiology 278.2 (2015): 563-577.

Huang, Yanqi, et al. "Radiomics signature: A potential biomarker for the prediction of disease-free survival in early-stage (i or ii) non-small cell lung cancer." Radiology 281.3 (2016): 1-11.

Jaffe, C. Carl. "Measures of response: RECIST, WHO, and new alternatives." Journal of Clinical Oncology 24.20 (Sep. 2016): 1-3.

Pan, Sinno Jialin, et al. "A survey on transfer learning." IEEE Transactions on knowledge and data engineering 22.10 (2010): 1-15.

Ruder, Sebastian. "An overview of multi-task learning in deep neural networks." arXiv preprint arXiv:1706.05098 (2017). 1-14.

Suk, Heung-Il, et al. "Deep learning-based feature representation for AD/MCI classification." International Conference on Medical Image Computing and Computer-Assisted Intervention. Springer, Berlin, Heidelberg, 2013. 583-590.

Woody, Neil M., et al. "A histologic basis for the efficacy of SBRT to the lung." Journal of Thoracic Oncology 12.3 (2017): 510-519.

DECISION SUPPORT SYSTEM FOR MEDICAL THERAPY PLANNING

RELATED APPLICATION

The present patent document claims the benefit of the filing date under 35 U.S.C. § 119(e) of Provisional U.S. Patent Application Ser. Nos. 62/677,716, filed May 30, 2018, 62/745,712, filed Oct. 15, 2018, which are hereby incorporated by reference.

BACKGROUND

The present embodiments relate to decision support for therapy. One typical example is the application in radiotherapy. Radiotherapy is a useful and cost-effective treatment strategy for many types of cancer. Although radiotherapy is an effective cancer treatment, a large portion of patients subsequently experience radio-resistance and recurrence of their cancers. Doctors seek to select treatments based on specific characteristics of the patient and their disease to avoid treatment resistance and recurrence.

Predictors of radiation response are largely limited to clinical and histopathologic parameters. Molecular characterization using genomic and proteomic technologies is limited due to spatial and temporal heterogeneity of tumors. The tumors usually require biopsies and invasive surgeries to extract and analyze small portions of tumor tissue, which does not allow for a complete characterization of the tumor. Medical imaging can provide a more comprehensive view of the entire tumor in an ongoing basis to monitor the development and progression of the tumor or its response to therapy. Imaging is noninvasive and is already often repeated during treatment in routine practice.

Predictive information personalized to a patient may be extracted from medical imaging. One example is the treatment selection for non-small cell lung cancer (NSCLC). Stereotactic body radiation therapy (SBRT) is the standard of care for medically inoperable patients with early-stage NSCLC. However, different patterns of failure (local recurrence or distant recurrence) can be observed after SBRT. Moreover, when patients undergo repeat SBRT or salvage therapy, the outcomes are significantly worse. Standard approaches for radiotherapy that demonstrate efficacy for a population may not achieve optimal results for individual patients. An unmet clinical need is to predict as early as possible the potential outcome. For instance, if the patients are divided into two groups of responders and non-responders based on some prognostic or predictive biomarker, a series of strategies could be followed to further change the response pattern. The treatment parameters or treatment sequence and modality may be changed in the treatment strategy for patients in the non-responder group.

In clinical practice, tumor response to therapy is only measured using one- or two-dimensional descriptors of tumor size (RECIST and WHO, respectively). Although the tumor size measured in follow-up scans can indicate response to therapy, it often does not provide enough predictive information to the outcome of therapy.

In radiomics, digital medical images are converted to high dimensional data for improved decision support. The hypothesis is that biomedical images contain information that reflects underlying pathophysiology and that these relationships can be revealed via quantitative image analyses. The practice of radiomics typically involves extraction and qualification of descriptive features from the volume and application of a model to predict outcome from the descriptive image features. In classical radiomic analysis, the image features that can describe various tumor physical and geometrical characteristics are pre-defined and can be computed using different mathematical formulas (handcrafted features). These features usually quantify characteristics about tumor intensity, shape, texture, and wavelet transformation focusing on the frequency domain. The radiomics analysis may fail to maximize the information obtained where a very large number of features are usually extracted from images which contain lots of redundant or irrelevant information. Handcrafted radiomic features are in pre-defined groups so it is likely that some predictive information is not fully captured by the pre-defined features.

SUMMARY

Systems, methods, and instructions on computer readable media are provided for decision support in a medical therapy. Machine learning provides a machine-learned generator for generating a prediction of outcome for therapy personalized to a patient. Deep learning may result in features more predictive of outcome than handcrafted features. More comprehensive learning may be provided by using multi-task learning where one of the tasks (e.g., segmentation, non-image data, and/or feature extraction) is unsupervised and/or draws on a greater number of training samples than available for outcome prediction alone.

In a first aspect, a method is provided for decision support in a medical therapy system. The support is in the form of outcome prediction personalized to a patient. A medical scan of a patient is acquired. A prediction of outcome from therapy for the patient is generated by a machine-learned multi-task generator having been trained based with both image feature error and outcome error. An image of the outcome (e.g., a therapy failure risk score) is displayed for decision support.

The medical scan may be of any modality, such as scanning the patient with a computed tomography scanner. The scan may have any spatial extent in the patient, such as acquiring voxel data representing a three-dimensional distribution of locations in a volume of the patient. The outcome is generated based on input of the voxel data for a segmented or other three-dimensional region of the volume.

Various embodiments are provided for generating the outcome. The machine-learned multi-task generator may be a convolutional neural network; may have been trained with deep learning to create features compared to handcrafted radiomics features for the image feature error; may have been trained with a greater number of training data samples for the image feature error than for the outcome error; and may have been trained with a weighted combination of the image feature error and outcome error as a loss function. The outcome error may be a cross-entropy loss or partial likelihood loss function, and the image feature error may be a mean square loss function.

The outcome may be a likelihood of therapy failure or tumor recurrence. The outcome may be an estimated time to reoccurrence or death.

In one embodiment, the machine-learned multi-task generator is used to identify one or more outlier samples in training data. The machine-learned multi-task generator may be retrained based on the identification of the outlier samples, such as by correcting, verifying, and/or removing the outliers.

The machine-learned multi-task generator includes an encoder for image features and a classifier for the outcome.

Due to the use of multiple tasks in learning, the acquired images and outcome generation may be for a first clinical problem, such as for a first organ, first tumor, and/or first diagnosis. Images may be acquired, and outcome generated for a different clinical problem, such as a different organ, using the same machine-learned multi-task generator. For any clinical problem, the patient is treated based on the generated outcome. Which therapy or the settings for therapy are selected using the predicted outcome, such as using an alternative where the outcome for a particular therapy to a particular patient is predicted to be poor.

In a second aspect, a method is provided for machine training decision support in a medical therapy system. A multi-task network is defined with an output layer for outcome estimation and an output layer for image feature estimation. A machine trains the multi-task network to estimate image features and to estimate outcome from input medical imaging volumes. The training is based on ground truth outcomes and ground truth (e.g., handcrafted) image features. The machine-trained multi-task network is stored.

The machine training uses a loss function including a weighted combination of an image feature loss and an outcome loss. The training uses training data samples for the ground truth outcomes and training data samples for the ground truth (e.g., handcrafted) image features. The training data samples for the ground truth outcomes are fewer in number than the training data samples for the ground truth (e.g., handcrafted) image features by an order of magnitude. The machine training may use training data with outliers removed or corrected. The outliers are identified by a previous iteration of the multi-task network.

In a third aspect, a medical imaging system is provided for therapy decision support. A medical imager is configured by software, firmware, and/or hardware to scan a patient. An image processor is configured to predict a result of therapy for the patient in response to input of scan data from the scan to a multi-task trained network. A display is configured to display the predicted result.

The medical imager may be a computed tomography imager. The multi-task trained network as applied was trained using a first loss for image features based on handcrafted radiomics and using a second loss for outcome.

In one embodiment, the multi-task trained network includes a machine-learned encoder for image features and a fully connected network for the prediction of the result (e.g., outcome) of the therapy.

In a fourth aspect, a method is provided for decision support in a medical therapy system. A medical scan of a patient is acquired, such as with a medical imager. A prediction of survival post therapy for the patient is generated by a machine-learned multi-task generator having been trained based on at least two losses including a survival loss. An image of the survival is displayed.

The medical scan may be of any modality, such as scanning the patient with a computed tomography scanner. The scan may have any spatial extent in the patient, such as acquiring voxel data representing a three-dimensional distribution of locations in a volume of the patient. The survival is generated based on input of the voxel data for a segmented or other three-dimensional region of the volume.

The machine-learned multi-task generator may be a convolutional neural network, such as an encoder network trained as part of an encoder and decoder network and a neural network configured to receive bottleneck features of the encoder network. The neural network generates the survival.

The other loss may be one of various losses, such as an image feature loss. For an image feature loss, the machine-learned multi-task generator was been trained with deep learning to create features compared to handcrafted radiomics features for the image feature loss.

The other loss is for a task providing a larger number of samples in the training data. For example, the machine-learned multi-task generator was trained with a greater number of training data samples for an image feature loss of the at least two losses than for the survival loss. The machine-learned multi-task generator may have been trained with deep learning including non-linear relationships between the survival and image features.

The survival may be a time to event or a likelihood as a function of time, such as a likelihood of reoccurrence by each time. In one embodiment, the survival loss used in training is a maximum likelihood. In another embodiment, the survival is stratified. The patient may be treated based on the stratification, such as treating if the likelihood of reoccurrence at a given time is below a threshold.

In a fifth aspect, a method is provided for machine training decision support in a medical therapy system. A multi-task network is defined to have an output layer for survival estimation and an output layer for image feature estimation. A machine trains the multi-task network to estimate image features and to estimate survival from input medical imaging volumes. The training is based on ground truth survivals and ground truth (e.g., handcrafted) image features. The machine-trained multi-task network is stored.

In one embodiment, the machine training uses a loss function including a weighted combination of an image feature loss and a survival loss, such as a maximum likelihood. The machine training includes training with training data samples for the ground truth survivals and training data samples for the ground truth (e.g., handcrafted) image features. The training data samples for the ground truth survivals are fewer in number than the training data samples for the ground truth (e.g., handcrafted) image features by an order of magnitude.

In another embodiment, the multi-task network is defined as an encoder and decoder with a neural network receiving bottleneck features of the encoder and decoder as input. The machine training includes comparing the ground truth (e.g., handcrafted) image features to an output of the decoder and comparing the ground truth survivals to an output of the neural network.

In a sixth aspect, a medical imaging system is provided for therapy decision support. A medical imager is configured to scan a patient. An image processor is configured to predict a time-to-event or failure risk after therapy for the patient in response to input of scan data from the scan to a multi-task trained network. A display is configured to display the predicted result.

The medical imager may be a computed tomography imager. The multi-task trained network may have been trained using a first loss for image features based on handcrafted radiomics and using a second loss for the time to event as survival. In one embodiment, the multi-task trained network includes a machine-learned encoder for image features and a neural network for the prediction of the time-to-event or failure risk after the therapy.

In a seventh aspect, a method is provided for decision support in a medical therapy system. A medical scan of a patient is acquired, such as from scanning a patient or from loading the scan from memory. A prediction of outcome of therapy for the patient is generated by a machine-learned multi-task generator having been trained based on a segmentation loss and an outcome loss. An image of the outcome is displayed.

The medical scan may be results or scan data from scanning the patient with a computed tomography scanner or other scanner. The acquired medical scan includes voxel data representing a three-dimensional distribution of locations in a volume of the patient. The outcome is generated based on input of the voxel data to the generator.

In one embodiment, the machine-learned multi-task generator is a convolutional neural network. For example, the outcome is generated where the machine-learned multi-task generator is an encoder network trained as part of an encoder and decoder network and a neural network configured to receive bottleneck features of the encoder network. The neural network generates the outcome.

In another embodiment, the machine-learned multi-task generator was trained with deep learning to create segmentations compared to ground truth segmentation for the segmentation loss and to compare prediction results to ground truth results for the outcome loss. The machine-learned multi-task generator may have been trained with a greater number of training data samples for an image feature loss of the at least two losses than for the survival loss.

In other embodiments, other types of data are input. For example, the generator is an autoencoder that generates the outcome in response to input of non-image data for the patient to the machine-learned multi-task generator.

Multiple generators may be trained. The machine-learned multi-task generator used for outcome prediction is selected from a group of trained networks, each of the trained networks corresponding to different combinations of types of input data.

In an eighth aspect, a method is provided for decision support in a medical therapy system. First non-image data representing characteristics of a patient is acquired. A prediction of outcome of therapy for the patient is generated by a machine-learned network having been trained as an autoencoder for generating second non-image data representing patients from third non-image data representing other patients. The second non-image data is of a same type as the third non-image data. An image of the outcome is displayed.

In one embodiment, the first non-image data is genomic, clinical, measurement, and/or family history data of the patient. The third non-image data is genomic, clinical, measurement, and/or family history data of the other patients.

The machine-learned network may be an encoder network trained as part of an encoder and decoder network and a fully connected network configured to receive bottleneck features of the encoder network, where the fully connected network generates the outcome.

In one embodiment, the machine-learned network was trained with multi-task deep learning to create segmentations compared to ground truth segmentation for a segmentation loss and to create outcome predictions compared to ground truth results for an outcome loss.

The machine-learned network may have been selected from a group of trained networks, where each of the trained networks corresponds to different combinations of types of input data.

In a ninth aspect, a method is provided for machine training decision support in a medical therapy system. A machine-training architecture is defined to have a plurality of data input options. Each data input option corresponds to a different type of data. The machine-training architecture is machine trained with different combinations of one or more of the data input options. The machine training with the different combinations results in different machine-trained generators configured to generate an output prediction for therapy. Performance of each of the machine-trained generators is determined. One of the machine-trained generators is selected based on the performance. The selected machine-trained generator is stored.

In one embodiment, the machine training is a multi-task operation with a loss function comprising a weighted combination of an image feature loss and an outcome loss. The machine-training architecture may be an autoencoder where the data input options include non-image data and a neural network configured to receive bottleneck features from the autoencoder. The neural network is trained to generate the prediction.

In other embodiments, the definition includes different types of data including image data cropped to tumors, a therapy dose map, image data in which the tumors are less than half a represented region, demographic data, and clinical data.

In a tenth aspect, a method is provided for decision support in a medical therapy system. A medical scan of a patient is acquired. A prediction of outcome of therapy for the patient from scan data of the medical scan is generated by a machine-learned multi-task generator having been trained with unsupervised learning from training data unlabeled for the outcome and having been trained from labeled training data for the outcome. An image of the outcome is displayed.

The patient may be scanned with a computed tomography scanner or other scanner. The medical scan may be voxel data representing a three-dimensional distribution of locations in a volume of the patient. The outcome is generated based on input of the voxel data to the generator.

In one embodiment, the machine-learned multi-task generator is an autoencoder having been trained with the unsupervised learning. For example, the training data is unlabeled for the outcome and includes tumor segmentation, non-image data, and/or radiomic image features. The autoencoder may be an encoder network trained as part of an encoder and decoder network and with the machine-learned multi-task generator including a neural network configured to receive bottleneck features of the encoder network for generating the outcome.

The machine-learned multi-task generator may be a fully-connected network configured to receive input from a bottleneck of the autoencoder where the fully-connected network was trained from the unlabeled training data.

In another embodiment, the outcome is generated in response to input of a scaled and intensity normalized version of the scan data and in response to input of a scale, intensity maximum, and intensity minimum for the version of the medical scan.

Therapy may be applied to the patient or not applied based on the outcome. To assist the decision to apply, image features from a bottleneck of an encoder of the machine-learned multi-task generator are clustered. Another patient is identified based on the clustering, such as finding a similar patient based on similarity of the bottleneck feature values.

In an eleventh aspect, a medical imaging system is provided for therapy decision support. A medical imager is configured to scan a patient. An image processor is configured to predict a result of therapy for the patient in response to input of scan data from the scan to a machine-trained network. The machine-trained network includes an encoder of an autoencoder trained in an unsupervised manner and a fully-connected network configured to receive an output of the encoder to predict the result. A display is configured to display the predicted result.

In one embodiment, the medical imager is a computed tomography imager. The machine-trained network may have been trained using a first loss for image features or segmentation and using a second loss for outcome.

In another embodiment, the machine-trained network is the encoder where the autoencoder was the encoder and a decoder to estimate an input from the output of the encoder in the training in the unsupervised manner. The fully-connected network may be a fully-connected multi-layer perceptron.

In other embodiments, the image processor is configured to cluster the output of the encoder and identify another patient based on the cluster of the output of the encoder.

In a twelfth aspect, a method is provided for decision support in a medical therapy system. A medical scan of a patient is acquired. Values for bottleneck features of a machine-learned autoencoder having been trained with unsupervised learning from training data unlabeled for a therapy outcome are generated. The values for the bottleneck features are clustered. Another patient is identified based on the values as clustered. Therapy data for the other patient is displayed.

The medical scan may be acquired by scanning the patient with a computed tomography scanner. The outcome may be generated with the machine-learned autoencoder being a multi-task generator configured to generate an output of therapy for the patient from the values for the bottleneck features.

Any one or more of the aspects or concepts described above may be used alone or in combination. The aspects or concepts described for one embodiment may be used in other embodiments or aspects. The aspects or concepts described for a method or system may be used in others of a system, method, or non-transitory computer readable storage medium.

These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

An imaging-based artificial intelligence provides for patient stratification and/or radiotherapy response prediction. This radiotherapy decision support may be based on pre-treatment CT or other modality scans. The therapy outcome may be predicted based on imaging and/or non-imaging data, providing physician decision assistance.

Figure 1:
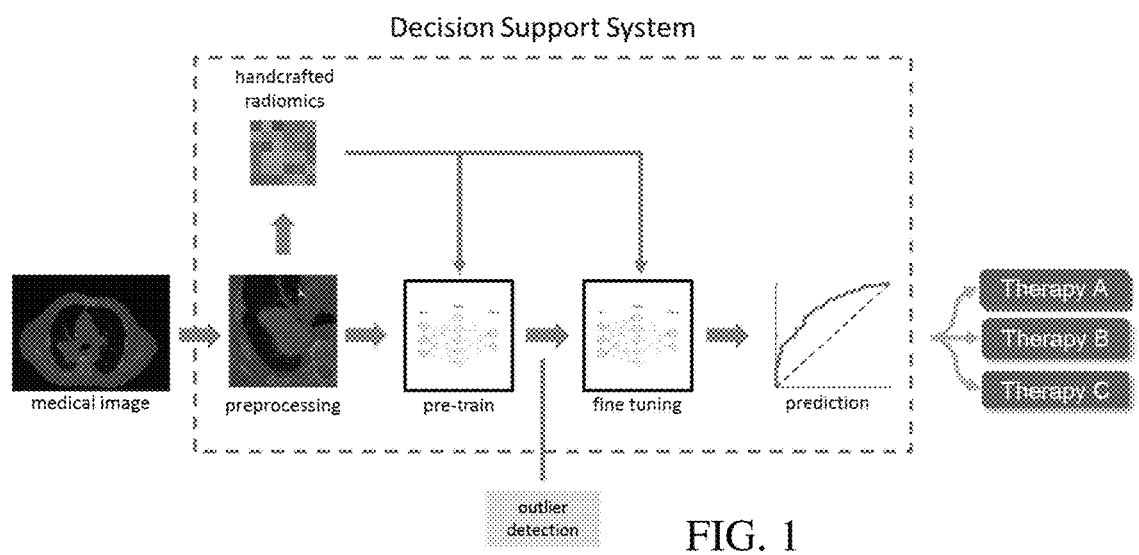
FIG. 1 illustrates an example of machine training a decision support system.

FIG. 1 shows one embodiment of a decision support system for producing prognostic signatures of the therapy from radiological imaging data. The signature is patient information or features from imaging data of the medical image. The medical image is preprocessed, such as scaled, normalized, and/or segmented for tumors or regions including tumors. Different from traditional radiomic features that are usually handcrafted, deep-learning-based radiomic features that are completely data-driven are to be used. The handcrafted radiomics are used as ground truth as these features may be created from any image, allowing for unsupervised learning or ground truth unlabeled for the outcome. A neural network is pre-trained to generate features based on the handcrafted radiomics as the ground truth for each image. Outliers in the dataset may be identified using the pre-trained network and verified as accurate, corrected, or discarded. The network is then fine-tuned using the training data with known outcomes as the ground truth. The network trained to generate features that lead to handcrafted radiomics is used to initialize or used with a network for predicting outcome. This decision support system may be used to stratify patients (e.g., predict outcomes of different therapies using the same or different trained networks) based on likelihood of therapy failure or likelihood of tumor recurrence post-treatment, and redirect the patients that have high risk of failure to an alternate or modified therapy regimen.

Figure 2:
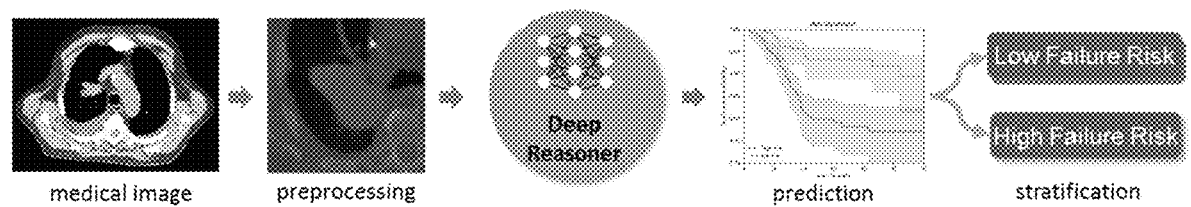
FIG. 2 illustrates another example of machine training a decision support system.

FIG. 2 shows another embodiment. In FIG. 2, a deep reasoner model, which is completely data-driven, is used for the prediction. The deep reasoner model utilizes artificial intelligence (AI) techniques to extract pertinent features (i.e., disease fingerprint) from patient imaging data acquired at a therapy planning phase. This task specific fingerprint is computed directly from imaging data of patients with similar disease and treatment. Thus, the deep reasoner only includes information closely related to the therapy outcome. These fingerprints are different from radiomics features as they are not generic measurements and are trained to be most discriminative for a specific condition or event. By fine tuning the network in a multi-task arrangement (outcome task and radiomic image feature task), the features generated for prediction outcome may be different than the handcrafted radiomics as the machine training identifies the image fingerprint information most discriminative of therapy outcome in the fine tuning. This AI-based image feature extraction may increase the accuracy of outcome prediction as compared to classifying from the handcrafted radiomics and as compared to classifying outcome using a singular outcome task. This AI-based image feature extraction may increase the accuracy of outcome prediction as there may be many more samples used in training at least part of the decision support system due to the use of ground truth that is based on the number of available images instead of the fewer number of samples with known outcomes.

In another embodiment, the decision support system provides decision support of radiotherapy treatment planning as follows: automated target structure contouring for radiotherapy (RT) or other therapy planning, prediction of the radiotherapy outcome from CT images in a planning phase, aggregating image and non-image features for therapy outcome prediction, and/or finding prognostic and predictive signatures for clinical decision support.

In one example, a therapy decision support system is provided for radiotherapy treatment planning. The input data includes radiomic, histologic and molecular features. This decision support system enables: selection of patients who benefit the most from a certain radiotherapy (e.g., compared to surgery, other radiotherapy, or other treatments), recommendation of optimal radiation dose of radiation, prediction of response to therapy (e.g. local control/likelihood of failure), and/or patient counseling and shared decision making. Any desired output may be provided by machine training a generator to create the output.

The decision support system of any of these embodiments may provide advantages compared to supporting decisions with handcrafted radiomics. The outcome prediction is automatic and data-driven with no bias introduced by human interaction. In the deep learning model, no manual feature selection is needed. The image features are not pre-defined based on the experience from other studies, so they are dedicated to each specific clinical problem. The prediction performance may be improved, providing more accurate decision support. Deep learning models can extract more features that do not exist in handcrafted radiomics. Also, unlike traditional calculated features, features of a convolutional neural network preserve a great deal of the global spatial information. The neural network provides a more robust estimation of the physical and geometrical characteristics of the tumor volume.

This additional information contributes to the improvement of prediction performance. A unified processing pipeline for various problems makes the system more efficient. By including some training using ground truth that may be extracted from the training samples themselves (e.g., handcrafted radiomics or segmentation), the decision support model is able to utilize the information in the vast amount of unlabeled data. For example, an auto-encoder is trained from unlabeled images in an unsupervised fashion. This is particularly useful when labeled data is scarce, a problem very common in the medical data domain due to high labor and financial cost in acquiring both the data and the labels.

An initially trained network may be used to automatically identify outliers from a large training database, effectively reducing labor cost in training. The same neural network architecture may be used for different problems (e.g., tumors in different organs) without changes. For new clinical problems, if the imaging modality is the same, the network does not need to be pre-trained, which saves more time for developing and deploying.

In another embodiment, the machine-learned generator of the decision support system projects the original high dimension image data into a low dimension space (e.g., bottleneck of an autoencoder, image-to-image network, or encoder-decoder network). The values of the features in the low dimensional space may be used as input to a fully connected or another network to predict the outcome. Alternatively or additionally, the values of the low dimensional space may be used to group patients in terms of predicted therapy outcome. An unsupervised clustering may be performed in this low dimension space to identify similar cases when an unseen case is presented. The prognosis of the patient may be more reliable when provided empirical cases of a similar nature.

The decision support model may output quantitative prediction of patients' response towards a certain therapy. Such predictive scoring is helpful in assisting physicians to make clinical decisions on therapy selection and prognosis. The clinical workflow in radiotherapy may be improved. The value of imaging in decision making, beyond diagnostics and therapy planning, may be increased, providing more information from already existing data. The example used herein is computed tomography images, but the idea can be applied to any imaging modality, such as ultrasound, magnetic resonance, single photon emission computed tomography, optical coherence, or positron emission tomography. With this decision support system, the clinician may improve their prediction rate of patient response to radiotherapy based on images.

Figure 3:
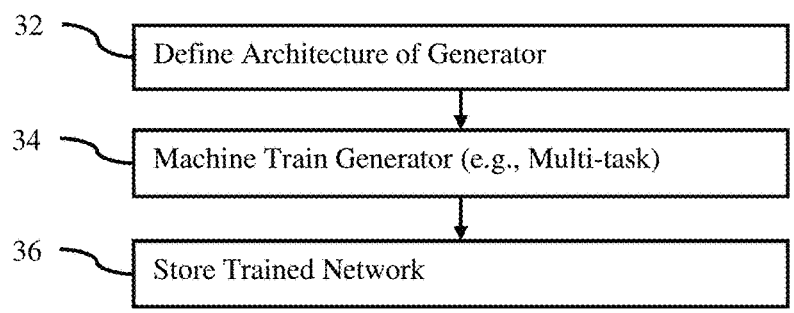
FIG. 3 is a flow chart diagram of one embodiment of a method for machine training decision support in a medical therapy system.
Figure 4:
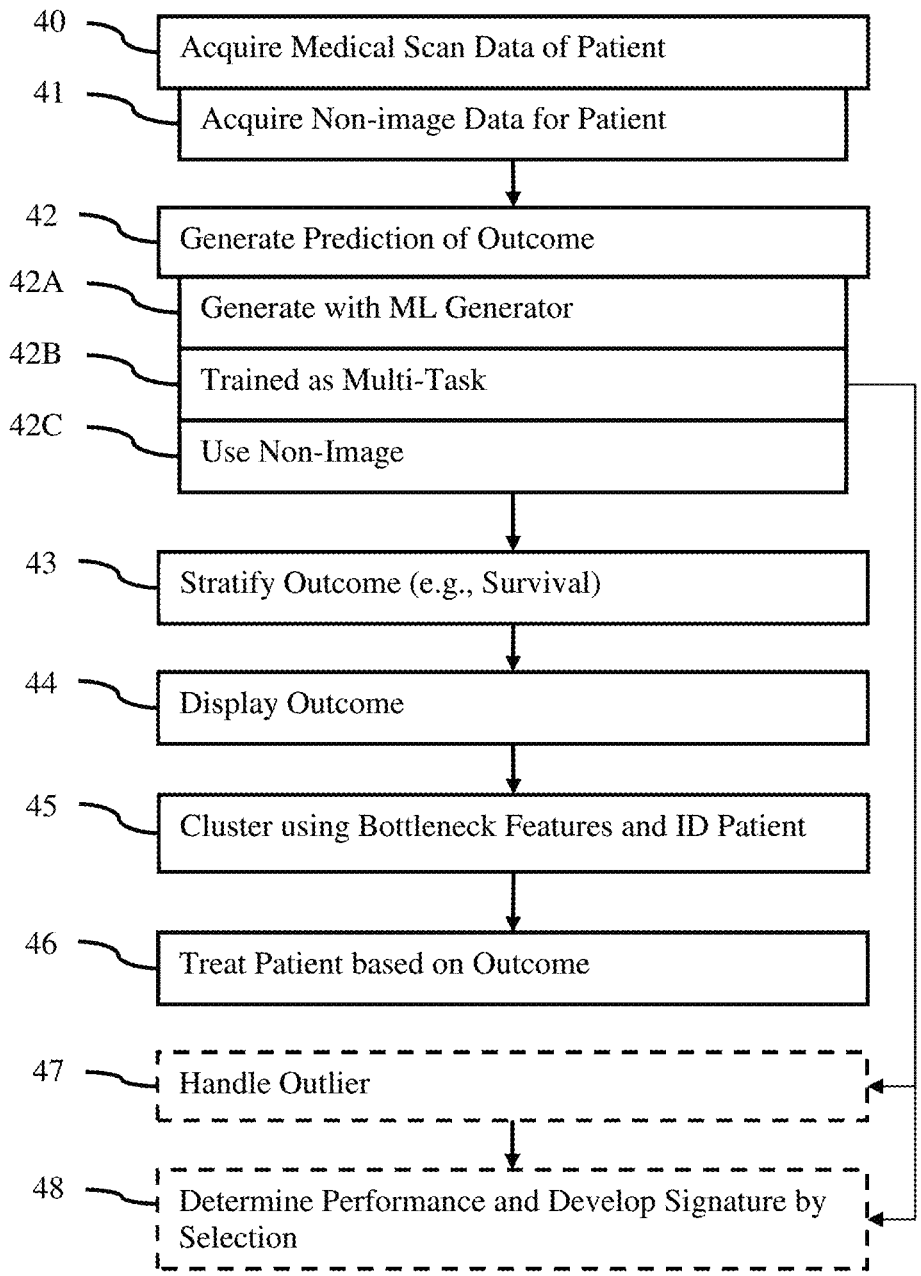
FIG. 4 is a flow chart diagram of one embodiment of a method for decision support in a medical therapy system.

FIG. 3 shows an example method for machine training the AI for the decision support. FIG. 4 shows a flow chart of one embodiment of a method for decision support using a trained network or generator. FIG. 3 addresses the training data and architecture in general as part of the definition for training. Various example multi-task networks as trained for outcome prediction and the training of the networks are discussed in conjunction with the application of FIG. 4. Examples provided for training of FIG. 3 may result in a trained generator for outcome usable in application of FIG. 4. Conversely, examples discussed in conjunction with the application of FIG. 4 may be trained as part of the training of FIG. 3.

FIG. 3 shows an example method for machine training decision support in a medical therapy system. The method is implemented by a machine (e.g., computer, processor, workstation, or server) using training data (e.g., samples and ground truths for the samples) in a memory.

The training trains a generator. Any machine-learning network or classifier may form the generator. The generator is trained to generate an output, such as an outcome prediction. For learning features as part of the training (i.e., deep learning), the generator is a neural network. Other networks or classifiers may be used.

The generator includes outputs for one or more tasks. For example, an autoencoder, image-to-image network, U-net, or convolutional neural network is used to output an estimation for one task. To provide more training samples to improve accuracy for prediction in the one task, the generator may be a multi-task generator. For example, a neural network is defined with an architecture having two or more outputs. A multi-task generator is used so that the generator is trained to optimize for the multiple tasks, such as including a loss function based on multiple losses (i.e., a loss for each of the tasks). The task having fewer samples in the training data may benefit (become more accurate while limiting overfitting) from the learning for the task with more samples.

In act 32, an architecture of the network to be trained is defined. In one embodiment, the architecture is defined as a multi-task architecture. The network architecture includes an output layer for each task, such as one output layer for segmentation or estimation of image features (e.g., hand-crafted radiomic features) and another output layer for outcome, such as survival or therapy results. Any generative architecture may be used for unsupervised learning to predict features, and any network architecture may be used for outcome prediction. For example, an image-to-image or generative adversarial network (GAN) network architecture is used, such as a U-net type of arrangement with down sampling and up sampling blocks or layers with or without skip connections. For multi-task in a GAN, the GAN includes two or more discriminator networks or layer arrangements. A discriminator network is provided for each task.

FIGS. 5-9, described below, show example embodiments of the network architecture. In one embodiment, the multi-task network is defined to include an encoder and decoder as an image-to-image network for generating a segmentation or image features from an input image for one task. The multi-task network is defined to also include a neural network for the outcome prediction, such as a neural network receiving as input bottleneck features output by the encoder to the decoder. For image features or segmentation, there may be many more samples available with ground truth (e.g., already known ground truth or later determined ground truth) than for outcome or survival. The training for each task benefits from the additional samples available for the other task. The training for outcome or survival, which has fewer samples with ground truth, benefits from the training for segmentation or image features, resulting in a more accurate prediction of outcome or survival. Other network architectures may be used, such as the classifier architecture for the outcome using the output of the decoder and/or receiving learned features from in the encoder or decoder (e.g., skip connections) as inputs.

For training the machine-learned network, the machine learning network arrangement is defined. The definition is by configuration or programming of the learning. The number of layers or units, type of learning, order of layers, connections, and other characteristics of the network are controlled by the programmer or user. In other embodiments, one or more aspects of the architecture (e.g., number of nodes, number of layers or units, or connections) are defined and selected by the machine during the learning.

In act 34, the machine (e.g., processor, computer, workstation, or server) machine trains the defined network (e.g., the defined multi-task generator). The network is trained to generate outputs for one or more tasks, such as multiple tasks. The generator and any discriminators are trained by machine learning. Based on the architecture, the generator is trained to generate output.

The training data includes many samples (e.g., hundreds or thousands) of input images (e.g., scan data to be used for imaging or images formatted for display) and ground truths. The ground truths may be annotations from experts or data mined from patient records, such as outcomes or segmentations for the samples. The ground truths may be automatically determined from the input, such as segmentation or radiomic features. The network is trained to output based on the assigned ground truths for the input samples.

For training any of the networks, various optimizers may be used, such as Adadelta, SGD, RMSprop, or Adam. The weights of the network are randomly initialized, but another initialization may be used. End-to-end training is performed, but one or more features may be set. The network for one task may be initially trained alone, and then used for further training of that network for the one task and a further network for the other task. Separate losses may be provided for each task. Joint training may be used. Any multi-task training may be performed. Batch normalization, dropout, and/or data augmentation are not used, but may be (e.g., using batch normalization and dropout). During the optimization, the different distinguishing features are learned. The features providing an indication of outcome and indication of another task are learned.

The optimizer minimizes an error or loss, such as the Mean Squared Error (MSE), Huber loss, L1 loss, or L2 loss. The same or different loss may be used for each task. In one embodiment, the machine training uses a combination of losses from the different tasks.

In one embodiment, the machine trains the multi-task network to estimate image features (e.g., radiomic features as a quantification of detected spatial distribution in an image) and to estimate outcome from an input medical imaging volume. Ground truth outcome is used to determine an outcome loss, and ground truth image features are used to determine an image feature loss. A loss function for optimization in the training is a weighted combination of the image feature loss and the outcome loss. The training may include retraining, such as using a learned generator to identify outliers in the training data. The multi-task network is retrained, fine-tuned, or trained again with the training data with outliers removed or corrected.

In another embodiment, the machine trains the multi-task network to estimate image features and to estimate survival from an input medical imaging volume. Ground truth survival (e.g., probability of survival over time, probability of recurrence over time, or a time to an event (e.g., recurrence)) is used to determine a survival loss (e.g., maximum likelihood loss). The ground truth survivals are compared to output predicted survivals of the multi-task network being trained. Ground truth image features are used to determine an image feature loss. Ground truth image features are compared to estimated image features output by an encoder in an image-to-image network. A loss function for training includes a weighted combination of an image feature loss and a survival loss.

In act 36, the trained network is stored. The network parameters, such as connections, convolution kernels, weights, or other learned values for the network are stored. The network is stored in memory to be used for application or testing.

Once trained, the generator may be applied to estimate an outcome of therapy for decision support. The many samples in the training data are used to learn to output given an unseen sample, such as a scan volume from a patient.

FIG. 4 is a flow chart diagram of one embodiment of a method for decision support in a medical therapy system. A machine-learned network or generator is used to estimate outcome for a therapy based on input data for a patient. For example, the outcome from radiotherapy for treating NSCLC is predicted. The outcome of other therapies may be predicted, such as chemotherapy, immunotherapy, etc. The outcome for a specific arrangement of settings or course of radiotherapy may be predicted. Different networks or generators may be used for different therapies for a same pathology and/or for different pathologies. In some embodiments, the outcome is predicated using a multi-task network or generator for more accurate outcome prediction than provided based on training for outcome alone.

The method is performed in the order shown (e.g., top to bottom or numerical), but other orders may be used. For example, acts 40 and 41 are performed in any order. As another example, act 44 is performed before act 43. Act 45 may be performed prior to act 43 or 44. Acts 47 and 48 may be performed prior act 43, such as part of using a machine-learned generator to select data used to then update or retrain the generator before application for a patient.

Additional, different or fewer acts may be provided. For example, acts 41, 43, 44, 45, 46, 47, and/or 48 are not performed. Acts 42B and/or 42C may not be used in some embodiments, such as where outcome is predicted with a machine-learned generator that is not multi-task and/or does not use non-image data.

The method is performed by a medical diagnostic scanner, a workstation, a server, or a computer. The scanner or memory are used to acquire data for a patient. An image processor, such as an image processor of the scanner or a separate computer, predicts the outcome, stratifies, and/or clusters. The image processor displays using a display screen or printer. A physician may use the output information to make a treatment decision for the patient.

In act 40, an image processor acquires a medical scan of a patient. The scan data from the scan of the patient is acquired from a medical scanner, such as a computed tomography scanner. The computed tomography scanner scans a patient with x-rays using an x-ray source and detector mounted to a gantry on opposite sides of a patient. A magnetic resonance, positron emission tomography, single photon emission computed tomography, or ultrasound scanner may be used. In alternative embodiments, scan data from a previous scan of the patient is acquired from a memory or transfer over a computer network.

The input of the decision support system is a medical image, such as scan data acquired at a therapy planning phase. The scan data represents an area or volume of the patient. For example, the scan data represents a three-dimensional distribution of locations or voxels in a volume of the patient. The distribution of locations may be in a Cartesian coordinate system or uniform grid. Alternatively, an non-uniform grid or polar coordinate format is used. For representing a volume, a scalar value is provided for each voxel representing the volume.

The scan data may be pre-processed before application to the decision support system or as part of the decision support system. Preprocessing may include segmentation, filtering, normalization, scaling, or another image processing. For example, one or more tumor volumes (e.g., gross tumor volume) or regions including the tumor with or without non-tumor tissue are segmented. The segmentation may be by manual delineation or automatically by the image processor. The scan data to be input represents just the segmented region or separate inputs are provided for the segmented region and the entire scan volume.

The pre-processed scan data (e.g., image data) is used alone to predict outcome. Alternatively, both the pre-processed scan data and scan data with more or less processing are input to predict outcome. Non-image data may be input instead or in addition to scan data.

In act 41, the image processor acquires non-image data. The non-image data is from sensors, the computerized patient medical record, manual input, pathology database, laboratory database, and/or other source. The non-image data represents one or more characteristics of the patient, such as family history, medications taken, temperature, body-mass index, and/or other information. For example, genomic, clinical, measurement, molecular, and/or family history data of the patient are acquired from memory, transform, data mining, and/or manual input. In another example, proposed therapy settings are acquired, such as a course of therapy including a sequence of therapy events, the power for each event, the duration of each event, and/or the region of application for each event.

In one embodiment, the decision support system includes a plurality of input modules. One input module is a network interface or buss to receive the medical image (e.g., scan data representing a volume). Another or the same input module receives other relevant medical information, such as blood test and histology images.

In act 42, the image processor generates a prediction of outcome from therapy for the patient. The prediction is based on input of the scan data (e.g., voxel data) and/or non-image data. For example, voxel data for a segmented three-dimensional region of a tumor and surrounding tissue is input.

The prediction uses artificial intelligence. A machine-learned generator, such as a machine-learned multi-task generator, predicts based on the input. The scan data and/or non-image data are input for the prediction, which is performed by artificial intelligence.

Act 42 is represented in FIG. 4 as having three components, generation with a machine-learned generator in act 42A, trained as a multi-task generator in act 42B, and using non-image data in act 42C. One, any two, all three, or none of these components may be used in various embodiments. In one embodiment, acts 42A and 42B (i.e., machine-learned multi-task generator) are used to predict the outcome.

Any machine-learned generator may be used. For example, a support vector machine, clustering, or other generator is provided for generating an estimate of the outcome based on the input. A machine-learned classifier may be used. In one embodiment, a neural network is trained as the generator, such as a trained convolutional neural network (CNN).

Various architectures may be used. The architecture defines the arrangement of layers, units, or other machine learning parts. For a neural network, the architecture may include one or more convolutional layers where the deep learning trains the kernel or kernels for filtering (convolution). Fully connected layers, max pooling layers, batch normalization, and/or other layers may be included.

The network is a deep architecture, which may include CNN or deep belief nets (DBN). Other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit. Skip connections, feeding values for features directly to layers in addition to or as well as a next layer, such as for a dense network.

Within a unit or layer, any number of nodes is provided. For example, 100 nodes are provided. Later or subsequent units may have more, fewer, or the same number of nodes. The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Max pooling, up sampling, down sampling, and/or softmax layers or units may be used. Different units may be of the same or different type.

In one embodiment, the architecture provides a multi-task generator or was trained as a multi-task generator (act 42B). Multiple outputs may be generated in response to the input. For application, less than all the trained network may be used, such as training as a multi-task generator but only using the parts of the multi-task network that output the outcome. Alternatively, the entire network or the parts that output the estimates for the different tasks are used.

Different parts of the network or architecture are trained for the different tasks. One part may be used for both tasks. One task is outcome. To assist in more accurate outcome prediction, another task is learned, such as unsupervised learning to segment (e.g., mask, extract, or label by location), generate radiomic image features, and/or generate non-image data. The outcome task uses features or part of the network trained for the other task.

Figure 5:
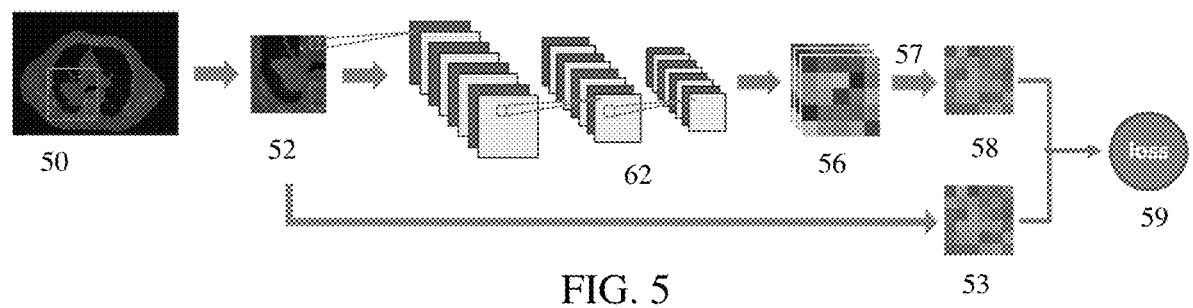
FIG. 5 shows an example machine-learning network for training using radiomic feature loss with a more commonly available ground truth than outcome.

For unsupervised learning to assist in learning for outcome, the machine-learned network may include an image-to-image network, such as a U-net, a generator of a generative adversarial network (GAN), or an autoencoder. This part of the network is trained to convert the input to a segmentation, non-image data, and/or radiomic features using unsupervised learning. FIG. 5 shows an example. Scan data 50 is input. The scan data is preprocessed at 52. The trained convolution units, weights, links, and/or other characteristics of the network 62 are applied to the data of the volume to extract the corresponding features through a plurality of layers and output the segmentation or radiomic image features. Within the network 62, deep-learned features of the input are extracted from the input. Other more abstract features may be extracted from those extracted features using the architecture. Depending on the number and/or arrangement of units or layers, other features are extracted from the input. The convolutional network 62 outputs image features 56. A fully connected layer 57 is used to convert image features to estimation radiomics 58. For training, the output radiomics or image features 58 are compared to features 53 extracted from the preprocessed scan data 52 to generate a loss 59 representing a difference between the handcrafted radiomic features 53 as ground truth and the output 58.

Figure 6:
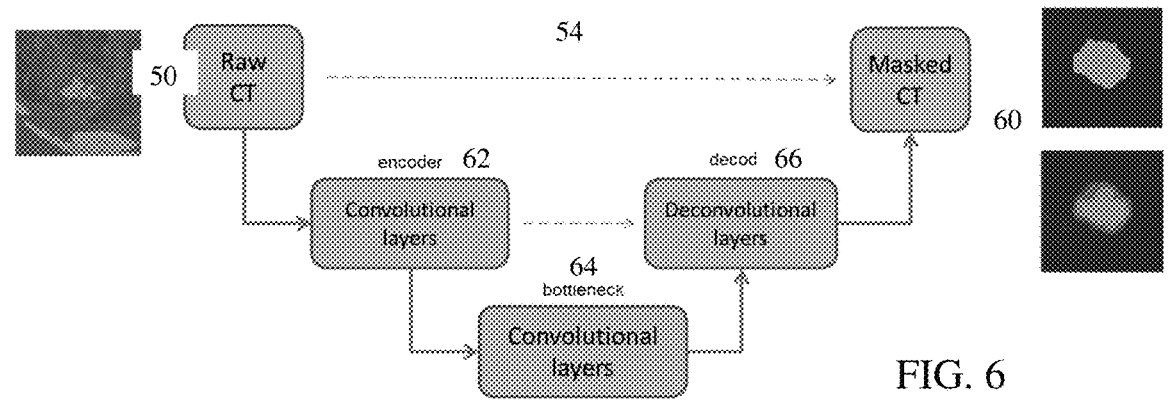
FIG. 6 shows another example machine-learning network for training using segmentation loss with the more commonly available ground truth than outcome.

FIG. 6 shows another example in the context of segmentation rather than radiomic image features. The scan data 50 is input to the network 54. In this example, a network 54 includes an encoder 62 and decoder 66 connected at a bottleneck 64. The bottleneck 64 may be a connection. In this example, the bottleneck 64 includes one or more convolution layers. The encoder 62 and decoder 66 include convolution layers. The decoder 66 outputs a masked volume, such as a segmentation. For training, this segmentation may be compared to ground truth segmentation to find the loss.

Any machine training architecture for outputting a spatial distribution from an input spatial distribution may be used for the segmentation or radiomic feature generation task. For example, U-Net is used. A convolutional-to-transposed-convolutional network is used. One segment of layers or units applies convolution to increase abstractness or compression. The most abstract feature values are then output as bottleneck features to another segment. The other segment of layers or units then applies transposed-convolution to decrease abstractness or compression, resulting in outputting of an indication of class membership by location. The architecture may be a fully convolutional network.

A GAN includes a generator, such as the image-to-image or U-Net, and two or more discriminators. A discriminator is provided for each task of the multi-task network. The generator includes an encoder (convolutional) network and decoder (transposed-convolutional) network forming a "U" shape with a bottleneck connection between passing features at a greatest level of compression or abstractness from the encoder to the decoder. Skip connections may be provided at other levels of abstract—feature values provided to the decoder from the encoder at a different level of abstractness than the bottleneck. Any now known or later developed U-Net architectures may be used. Other fully convolutional networks may be used.

For application for a given patient, the generator of the GAN is used without the discriminators. The discriminators are used for training. For an image-to-image or autoencoder, the encoder may be used without the decoder in application. Alternatively, the entire network is used. For training, a simpler form of the model that uses only an encoder and a classifier but without a decoder may be constructed and trained. This encoder only in training may require more labeled data because the model lacks the capacity to utilize the information from the unlabeled data in an unsupervised fashion.

The machine-learned multi-task generator includes a classifier part for the outcome prediction task. Any machine learning architecture for outputting the outcome may be used. For example, a classifier is trained to output the outcome. A neural network, such as a convolutional neural network, outputs the outcome. At least one layer, unit, or other part of the network for another task (e.g., segmentation or radiomic feature generation) is used in the outcome prediction. For example, the output of the decoder is used by separate layers for generating the outcome. In another example, the output of the encoder is used, such as a neural network or other classifier receiving feature values from the bottleneck 64 as inputs to output the outcome estimate.

In another embodiment, the output or final layer of the architecture may form both outputs. One network may be used for both tasks. There are multiple outputs from the one network. There is one output for the segmentation or radiomic feature generation task and another output for the outcome estimation. One or more additional layers may be added in this framework to further process an output for one task to generate an output for another task.

In one embodiment, the multi-task generator used in application is an encoder network trained as part of an encoder and decoder network, and a convolutional neural network configured to receive bottleneck features of the encoder network for generating the outcome or survival. The multi-task learning is used to train the encoder-decoder and CNN. Other arrangements or architectures may be used.

Figure 7:
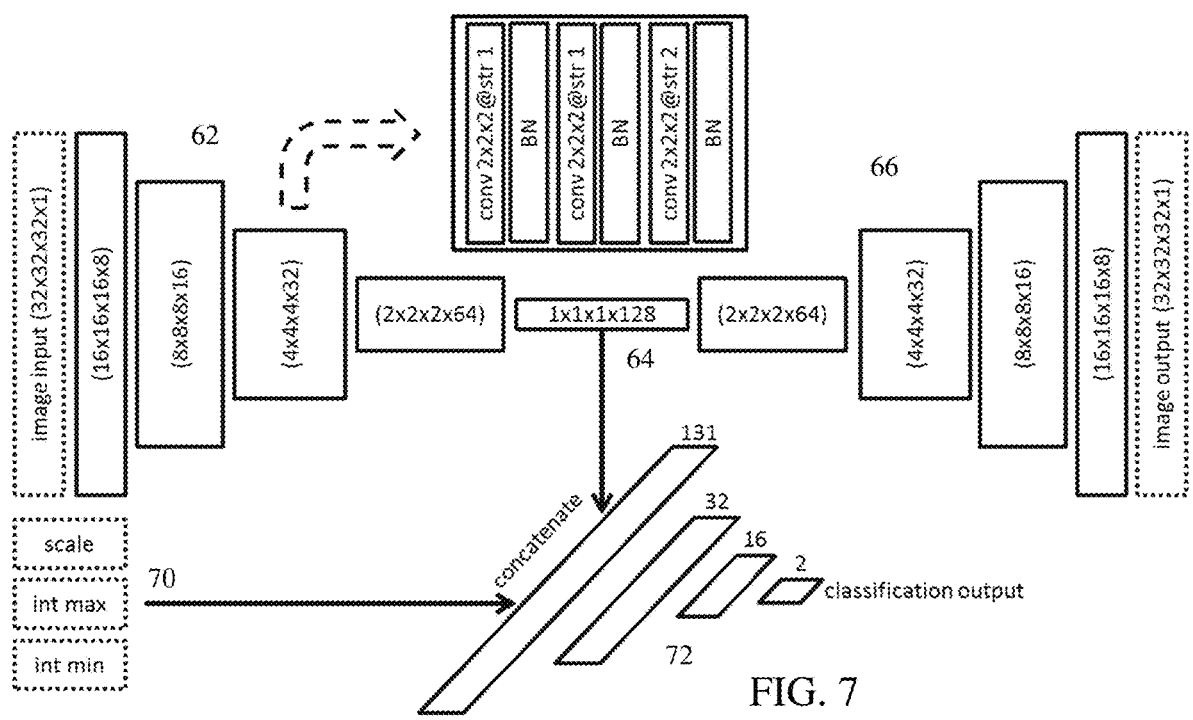
FIG. 7 shows an example machine-training architecture for a multi-task generator.

FIG. 7 shows an embodiment with the network architecture including the encoder 62, bottleneck 64, and decoder 66 (e.g., together forming an autoencoder) used to train for segmentation or radiomic feature estimation. For application, the decoder 66 may not be used. For outcome prediction, the network architecture includes a convolutional neural network 72 connected to receive output of the encoder 62 or the bottleneck 64 as input and output a binary classification of outcome. The number of input feature values for each layer is shown above each layer in FIG. 7. In the artificial intelligence predictive module, a deep neural network 54 of the encoder 62 and network 72 is a model to extract high level features from 3D lung CT images. The auto-encoder model 54 feeds the features to a fully-connected classification model 72 to harness information from the vast amount of unlabeled data as well as the limited amount of labeled data.

In one embodiment, the auto-encoder network 54 (encoder 62, bottleneck 64, and decoder 66) includes units (e.g., each rectangle) having three 3D convolutional layers and three batch normalization layers, as illustrated in the center top box indicated by the dashed arrow. The input image is of dimension 32×32×32×1 at the beginning, gradually shrinks to a bottle-neck vector of 1×1×1×128 as convolutions are operated, and gradually grows back a dimension of 32×32×32×1 with deconvolution operations. The classifier part (CNN 72) takes in the bottleneck latent variable of 1×1×1×128. The input image is scaled and normalized in preprocessing. To account for the scaling and normalization, values for the scale and the maximum and minimum intensities of the original image 50 are input 70 to the classifier part with the bottleneck features. The classifier part is a fully-connected multi-layer perceptron, which outputs the predicted outcome as a binary class membership. Other resolutions, input variables, vector sizes, numbers of units, layers in units or variation across units may be used.

Figure 8:
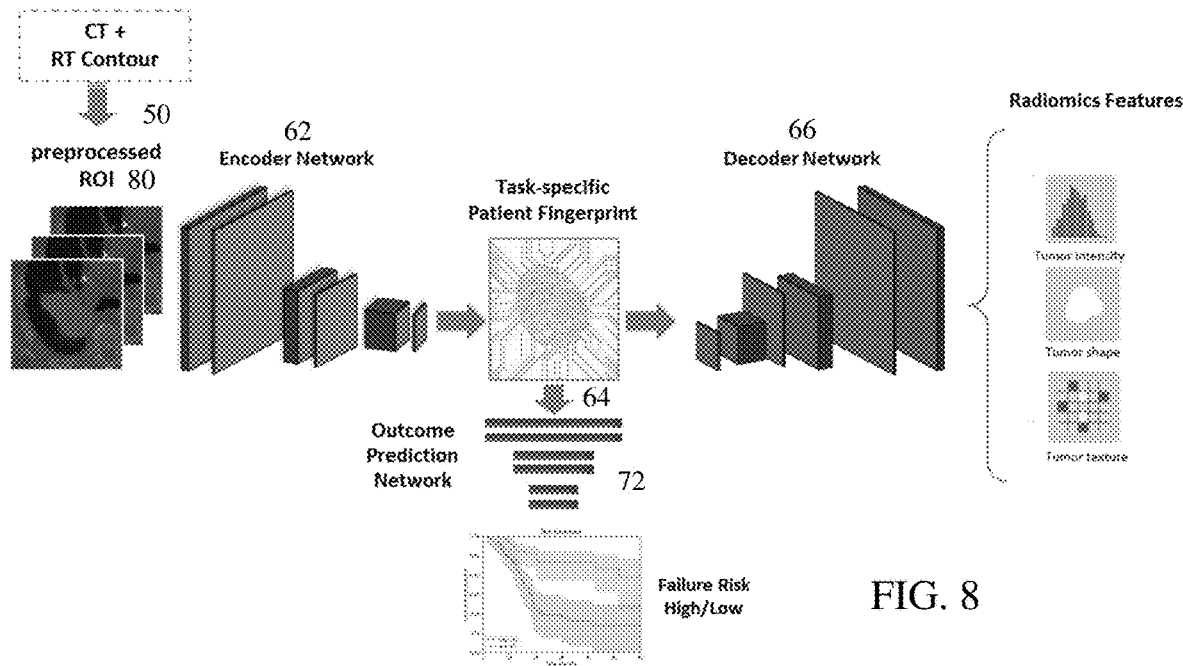
FIG. 8 shows another example machine-training architecture for a multi-task generator.

FIG. 8 shows an embodiment with application of the network architecture of FIG. 7 or a similar network. The scan data 50 and a therapy contour are input. The scan data is preprocessed (e.g., segmented region of interest 80), so the preprocessed scan data and radiotherapy contour are input to the encoder 62. The decoder 66 is trained to output radiomic features, such as tumor intensity, tumor shape, and/or tumor texture features. The neural network 72 is trained to output a risk of failure as a risk over time or probability distribution rather than a binary outcome.

The machine-learned, multi-task generator predicts outcome in response to input of the scan data. For example, personalized radiotherapy outcome is predicted from CT images of a tumor of a patient in a therapy planning phase. Unlike current radiomics methods that use pre-defined features for all tasks, the deep learning trains the generator to directly extract high-throughput image features. Since the features are created based on the specific task, the features may be more accurate and informative than general quantitative image measurements for therapy outcome prediction. In the example of FIGS. 7 and 8, the network 54 is a CNN arranged as an encoder network 62 to build the sought-after task-specific fingerprint (features). The fingerprint in this case is based on a set of latent variables at the bottleneck 64 of the overall encoder and decoder network 54.

The outcome is generated by a machine-learned multi-task generator that was trained based on both image feature error and outcome error. Deep learning was used to both create features for comparison to handcrafted radiomics features and create outcome for comparison to ground truth outcome. In alternative embodiments, other data sources for unsupervised learning and corresponding error are used, such as segmentation instead of handcrafted radiomics features.

In one embodiment, the machine-learned multi-task generator was pre-trained using the handcrafted radiomics. Just the portion of the network for unsupervised learning or learning from the radiomic features or segmentation is initially trained. In the computer vision domain, transfer learning and fine tuning are often used to solve the problem of a small dataset. The part of the network is pre-trained for the clinical problem (e.g., using 3D CT image of the lung for NSCLC). The machine-learned multi-task generator was then fine-tuned by training for multiple tasks (see FIG. 1). The multi-task learning network was trained for both radiotherapy segmentation or radiomic features and outcome prediction problems using a combined loss. Many imaging features (e.g. texture or segmentation) are informative to both tasks. By sharing representations between related tasks, the model generalizes better on both original tasks.

In one embodiment, one task is to generate handcrafted radiomic features (see FIG. 5). In another embodiment, the task is to generate a segmentation. The machine-learned multi-task generator generates prediction of outcome of therapy for the patient by having been trained based, in part, on a segmentation loss and an outcome loss. FIG. 6 shows the part of the machine-learned multi-task generator trained to generate segmentation, such as labels by voxel of membership, fitting of a boundary, and/or extraction of a sub-region. This part was trained with deep learning to create segmentations compared to ground truth segmentation for the segmentation loss. For fine tuning, the machine-learned multi-task generator was trained to compare segmentation to ground truth and to compare prediction results to ground truth results for the outcome loss.

For the segmentation embodiment, automated target structure contouring is provided for radiotherapy planning. A segmentation model is built using planning computed tomography images and different radiotherapy contours (i.e., ground truth segmentation). For example, the input of the network is a computed tomography image (e.g., 3D scan data) that includes gross tumor volume (GTV) and neighboring tissues. The ground truth target image is a mask of a selected ROI, so the output of the network is a GTV heatmap. In FIG. 6, the architecture is an U-Net convolutional network architecture to achieve a fast segmentation of images. Other kinds of fully convolutional networks may be used for segmentation. Semi-supervised convolutional neural networks, recurrent neural networks, unsupervised clustering, or reinforcement learning may be adopted for further refining the segmentation.

Autocontours (automatic segmentation) may reduce the inter-observer and intra-observer variability in target delineation, reduce contouring time, and thus improve the quality of radiotherapy, so the entire part may be used in application to provide segmentation. The encoder network architecture and parameters used for segmentation (e.g. encoder and bottleneck layers of a UNet) may be used for initializing a feature extraction network (i.e., train the network of FIG. 6 to initialize the network of FIG. 5). The model used for segmentation may also be used as a pre-trained network for outcome prediction to overcome the smaller number of samples of outcome ground truth. Alternatively, the machine-learned multi-task generator was trained initially for both outcome and segmentation or feature generation.

Due to use of the segmentation or radiomic features represented in the scan data, there may be many samples available. Any scan may be used as a sample since the ground truth may be extracted from the scan data. Conversely, outcome may not be determined without expert or manual review of patient records. It may be difficult to determine outcome for any given patient, so there may fewer samples of outcome ground truth. The machine-learned multi-task generator may have been trained with a greater number of training data samples for the image feature or segmentation error than for the outcome error due to the availability of data. Alternatively, there are an equal number of samples or more samples for outcome than for image features or segmentation.

When the data sets are large enough, the deep learning algorithms and encoder-decoder architectures often perform much better compared to traditional algorithms. In the medical image analysis domain, the datasets for outcome are often inadequate (e.g., too few samples such as a few hundred) to reach full potential of deep learning, resulting in overfitting problems. This is more likely to happen in the therapy outcome prediction problems due to the lesser number of samples. For all the patients treated with radiotherapy, the pre-treatment imaging and corresponding tumor delineations are often available, but the therapy outcomes are often missing because of limited follow-ups. To fully utilize the entire dataset, especially images without outcome labels, the multi-task architecture (e.g., a CNN-based regression model to estimate the physical and geometric properties of the tumor volume and a classifier) is used.

FIG. 5 illustrates one instance of this process, applied to planning computed tomography scans of stereotactic body radiation therapy (SBRT) for non-small cell lung cancer (NSCLC) patients. Similar as handcrafted radiomics, the network takes the preprocessed computed tomography image, with gross tumor volume (GTV) annotated, as input and generates a set of image features 56. The fully connected layer 57 is used to connect the image layer 56 and the regression layer 58, which is the output of the network. The output 58 is an estimation of the radiomic features and is compared with handcrafted radiomics 53. The error between the estimated radiomics and handcrafted radiomics is used as the loss for training the network. Since radiomic features have different physical meanings and units, the radiomic features are normalized or different weights are set for induvial features in determining the loss.

Given that handcrafted radiomics are a relatively efficient yet generic representation of tumor phenotype (e.g. size, shape, texture, etc.), the decoder network 66 of the network 54 reconstructs radiomic features from latent fingerprint variables. The fingerprint in this case is going to be able to reconstruct a full set of radiomics features, and thereby the entire network 54, 72 is more constrained and regularized and as the results is less susceptible to overfitting. Traditional radiomics or segmentation constrain the network 54, 72 to alleviate overfitting. The multi-task learning framework adds constrains on the neural network image features, so that image features keep the physical properties of the tumor volume.

The machine-learned multi-task generator generates the outcome of therapy by having been trained with unsupervised learning from training data unlabeled for the outcome and having been trained from labeled training data for the outcome. The autoencoder, U-net, image-to-image network, or encoder-decoder network was trained with unsupervised learning to provide many samples since the scan data may be unlabeled for the outcome. The unsupervised learning may be based on tumor segmentation, non-image data, radiomic image features, and/or other data available for many samples. The fully-connected network 72 for outcome prediction was trained from the labeled training data and the unlabeled training data.

The machine-learned multi-task generator was trained with a combination of losses. For example, a weighted combination of the image feature error and outcome error is used as a loss function for training. Any combination may be used for the joint learning or losses for the different tasks. The resulting machine-learned multi-task generator may better predict outcome due to the use of multiple losses in training.

Two or more tasks are trained simultaneously. The main task is the outcome prediction. Any loss function may be used for outcome loss or error. For example, a cross entropy loss function $L_1$:

$$L_1 = \sum_{c=1}^{M} y_c \log p_c$$

is used, where M is the number of different outcomes, y is a binary indicator (0 or 1) if class label c is the correct classification for the observation, and p is the predicted probability observation of class c. Other loss functions, such as a partial likelihood loss or another function for a continuous output variable rather than binary class membership, may be used.

The auxiliary task is the estimation of handcrafted radiomics, segmentation, or non-image data. Any loss function may be used for the segmentation or image feature loss or error. For example, a mean square error between the network output 58 and handcrafted radiomic feature values 53 is used. The mean square loss function $L_2$ may be represented as:

$$L_2 = \sum_{d=1}^{n} (y_d - o_d)^2$$

where n is the number of radiomic feature dimension, y is the handcrafted feature value, and o is the network output value at dimension d. Other loss functions may be used.

For simultaneous training, a combination of the task losses is provided. For example, the total loss is a weighted combination of two tasks:

$$L = \lambda_1 L_1 + \lambda_2 L_2$$

The weights λ are hyper-parameters that determine whether to keep more handcrafted information for the outcome prediction. Other combinations may be used, such as a ratio.

Figure 10:
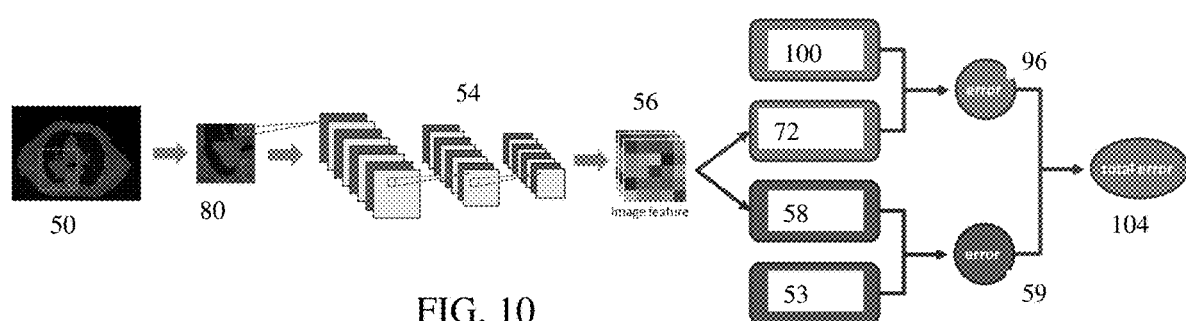
FIG. 10 shows another example of use of two losses in training a multi-task generator.

FIG. 10 shows an example of the combination. A network output of radiomic features 58 are compared to the ground truth handcrafted radiomic features 53 to provide the feature error 59. The outcome from the network 72 is compared to a ground truth outcome 100 to provide the outcome error 96. The outcome error 96 and the feature error 59 are combined into a total error 104.

Figure 9:
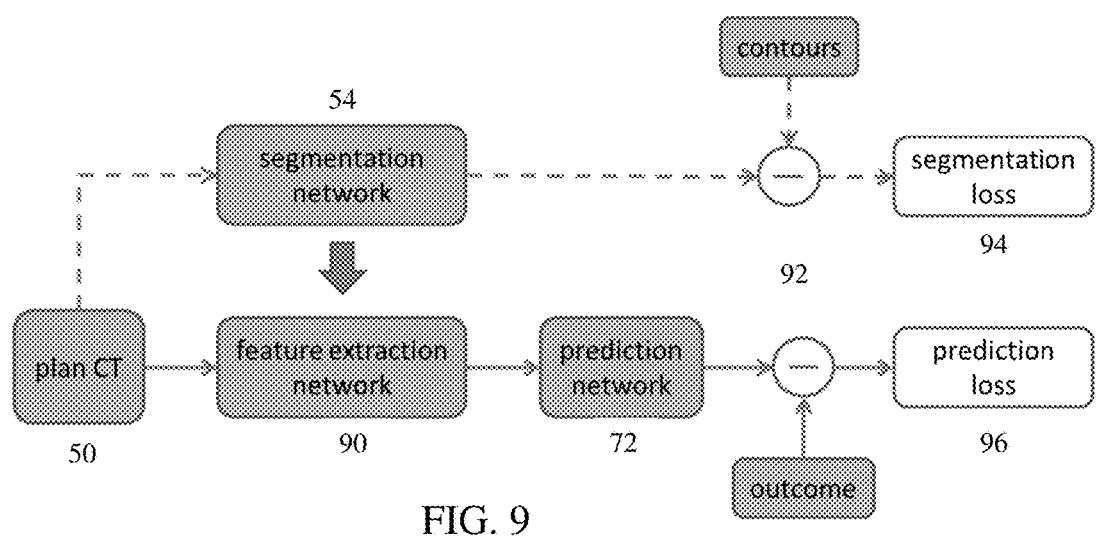
FIG. 9 shows an example of use of two losses in training of a multi-task generator.

FIG. 9 shows another example using segmentation as the secondary task instead of image features. This secondary task and corresponding loss add constraints and regularity to the neural network for the primary outcome task so that the fingerprint can reconstruct radiomics features yet be performant enough to estimate the outcome for each patient. Segmentation network 54 may be pre-trained. For fine tuning, losses for multiple tasks are used. The segmentation network 54 provides features for outcome prediction, represented as feature extraction network 90. The feature extraction network 90 may be the encoder 62 of the segmentation network 54. For example, bottleneck feature values from the segmentation network 54 are provided to the prediction network 72. The output segmentation is compared 92 to the ground truth contours to provide a segmentation loss 94. The output outcome is compared 92 to the ground truth outcome for the prediction loss 96. The segmentation loss 94 and prediction loss 96 are combined for training using multi-task learning.

The outcome prediction has a loss function in the form $L_1 = \mathcal{L}(\theta)$. The auxiliary task is the estimation (reconstruction) of segmentation, which is formulated as a mean square loss function $L_2$. The total loss is a weighted combination of the two tasks.

The outcome is predicted as a likelihood of therapy failure or success. The success may be based on lack of increase in size or tumor being gone. The success may be a measure at a given time after therapy. The outcome may be for tumor recurrence. Any measure of therapy outcome may be used. The prediction is a binary determination. Alternatively, a probability for the binary determination is provided.

By predicting the outcome, the physician can determine whether a given therapy may be appropriate for a given patient. The prediction may be for outcomes for more than one type of therapy so that the physician may select the more likely to be successful therapy. The same or different machine-learned multi-task generator makes the prediction for the different therapies.

In one embodiment, the outcome is predicted as a survival. Rather than a binary prediction, the prediction may be of a continuous variable, such as probability of survival as a function of time. The survival may be a time-to-event (e.g., 28 months). The time-to-event may be a time between treatment and recurrence of the tumor at a local region, a time between treatment and recurrence of the tumor in any region (e.g., local, nodal, or distant given by a progression free survival time), and/or a time until death. The machine-learned multi-task generator predicts survival for the patient and/or tumor post therapy. The survival is predicted based on the generator having been trained on a survival loss as the outcome loss.

Deep neural network models are commonly used to solve classification problems. In survival prediction dealing with therapy outcomes on a set of events in time, binary labels are created by setting a threshold on time to a certain adverse event value. The problem with setting a threshold on time to event variables is twofold: 1) the threshold itself is rather subjective and its variability has significant effect on overall results and needs to be taken somehow into account, and 2) due to censoring (i.e., loss of follow-up or occurrence of a competing event), a lot of data may need to be discarded as the true label cannot be known. In order to address these issues, survival analysis or a time-to-event approach is used in the prediction.

Survival analysis is usually used in medical studies to evaluate the significance of prognostic variables in modeling the time that elapses from the beginning of an observation period, such as beginning treatment, until the occurrence of an event of interest like death or occurrence of a disease. One standard survival model is the Cox proportional hazards model, which assumes the risk of failure is a linear combination of all covariates. In many conditions, a linear combination may be too simplistic. A neural network may learn highly complex and nonlinear relationship between a prognostic set of variables. Deep learning extends the regular linear Cox regression to a nonlinear form. Like the Cox model, deep learning is also a non-parametric model, which in general means that there are no assumptions made about the form of the baseline hazard function. The ratio of the hazard for an individual on a new treatment to that for an individual on the standard treatment is assumed to remain constant over time, but the logarithm of the hazard ratio is no longer a linear form of covariates. The machine-learned multi-task generator may have been trained with deep learning, which allows for non-linear relationships between the survival and image features or segmentation.

Since survival may be a continuous variable (e.g., time until X), the loss function may be different than used for a binary classification. For example, the survival loss is a maximum likelihood instead of a binary cross-entropy. To fit the model, the coefficient is estimated using the maximum likelihood method in much the same way as done with Cox regression. In order to train the network to regress the time-to-event, the loss function accounts for the various variables and the continuum of the output variable. Assuming k different variables (or image voxels) for each patient i, $X_i = (x_1, x_2, \ldots, x_k)$, the loss function of the prediction network is a negative log partial likelihood of all samples in the training dataset, represented as:

$$\mathcal{L}(\theta) = -\log \prod_{i=1}^{n} \left[ \frac{\exp\{\varphi_\theta(X_i)\}}{\sum_{j=1}^{n} Y_{ij} \exp\{\varphi_\theta(X_i)\}} \right]^{\delta_i}$$

Other loss functions may be used.

In another embodiment, non-image data is used instead of or with segmentation and radiomic features. The machine-learned multi-task generator generates the outcome in response to input of non-image data for the patient. The machine-learned multi-task generator was trained as an autoencoder to output non-image data based on input of non-image data. The output for the unsupervised learning part is of the same type of information as the input. The neural network is trained to extract features that allow for predicting the output as the same as the input.

Non-image data may be more widely available than outcome. For example, non-image data includes genomic, clinical, measurement, and/or family history data. Such data may be obtained from the computerized medical records of many other patients In another embodiment, image and non-image features are aggregated for therapy outcome prediction. For example, segmentation and/or radiomic features are combined with non-image features for outcome prediction. Feature vectors may be created from each type of data (e.g. genomics, clinical), and the feature vectors are concatenated as a new feature vector. By using a deep autoencoder, the input may be any form of data and the output is the same as the input but reconstructed from intermediate low dimensional representations or network-learned features. The low dimensional representations may be integrated as the input of the network 72 for outcome prediction. The autoencoder network 54 is an unsupervised learning method so may be trained without therapy outcome labels.

Returning to FIG. 4, the image processor stratifies the predicted outcome in act 43. The binary classification may not be further stratified as the class defines the group membership. For survival, the time-to-event or other continuous variable may be stratified. For example, a threshold is used to group patients into two groups—survival of less than two year and survival of more than two years. Three or more groupings may be used for stratification. The stratification may assist in relative comparison to a guideline or standard. In alternative embodiments, stratification is not performed.

In act 44, a display displays an image of the outcome. The display is a visual output. The image processor generates an image. The image may be output to a display, into a patient medical record, and/or to a report.

The outcome may be an annotation, alphanumeric text, graph, or chart. For example, the survival is displayed as a graph of survival probability as a function of time. As another example, stratification results are displayed. The output may be a single image signature that is predictive of therapy outcome. The prediction score is projected to the display for the physicians.

The radiomic feature values, segmentation, and/or non-image data estimated by the machine-learned network may be output. Other information may be displayed with the predicted outcome, such as input information. More than one prediction may be output, such as outcome predictions for different therapies.

The outcome may be presented with or on (e.g., overlay or annotation) an image of the patient. For example, an image of a slice through a tumor region is displayed. The outcome is provided with the image of the anatomical structure of interest, such as the lung or gross tumor volume, on a display screen. Where 3D scan data is provided, the 3D scan data is rendered to a 2D plane. Any rendering may be used, such as projection rendering.

Figure 11:
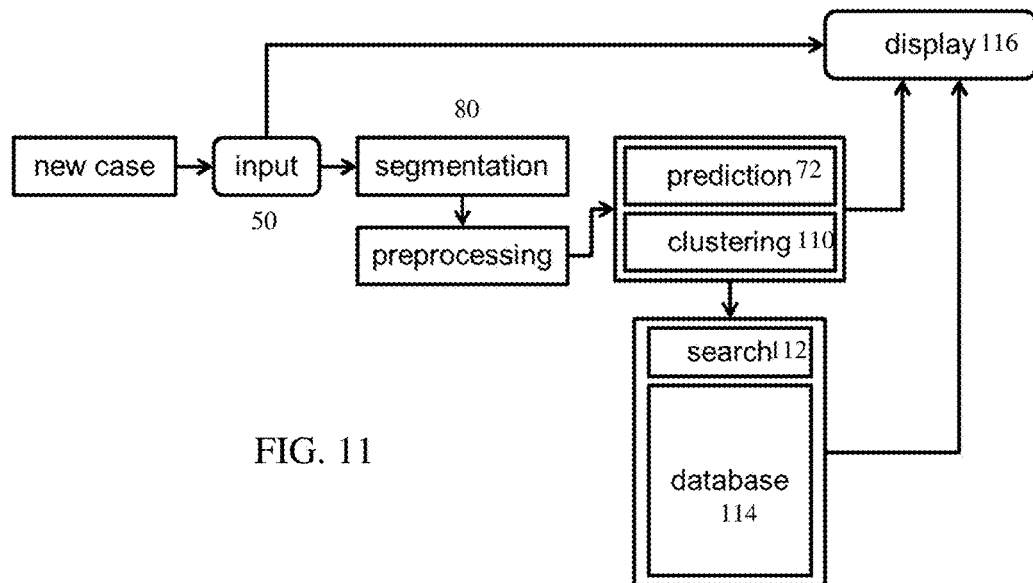
FIG. 11 is one embodiment of an arrangement using both prediction of outcome and clustering in decision support.

The display may include information from one or more similar patients. Given the large number of variables available for a patient, it may be difficult to identify similar patients. In act 45, the machine-learned multi-task generator is used to select similar patients. To reduce the number of search parameters, deep learned features may be used for similarity matching. For example, the image features from the bottleneck of the image-to-image network (i.e., output of the encoder) are used to identify one or more other patients based on clustering 110 as shown in FIG. 11. After segmentation 80 and any other preprocessing, the autoencoder or image-to-image model may cast the high dimensional image data into a low dimensional space to perform classification by the outcome prediction network 72. The values from the low dimensional space may be used for clustering 110. The training data provides samples for other patients. The training may provide the values for the bottleneck features for these different samples in a database 114. Clustering 110 is used to simplify the search 112 for similar patients. The identified patient or information about identified patient is displayed 116.

In one embodiment, the machine-learned multi-task generator generates values for bottleneck features of a machine-learned autoencoder having been trained with unsupervised learning from training data unlabeled for a therapy outcome. Alternatively, the machine-learned generator is not a multi-task generator but is an autoencoder or another encoder-decoder network. The values are clustered. Any grouping or clustering approach may be used, such as K-Means clustering, Gaussian Mixture Models (GMM) or spectral clustering. The clustered values are used to identify another patient. Clusters of bottleneck values for a representative sampling of other patients are compared by a search engine to the cluster for the patient. Any comparison may be used, such as Euclidean distance in the high dimensional space or Pearson correlation distance. Data for a most or sufficiently similar patient is displayed for decision support to assist in therapy planning. Images, therapy outcome, and/or other data for one or more similar cases are projected onto the display for the physicians to provide empirical information during the decision-making process.

In act 46, the physician treats the patient. The physician uses information about the patient and the output outcome to select a therapy or to not select a therapy. The stratification, survival, and/or other outcome are used to select the treatment for the patient. For example, the outcome for radiotherapy is predicted to be positive or stratifies to a positive level, so radiotherapy is selected where there are no counter indications. As another example, the physician selects radiotherapy or radiotherapy with particular settings or course of application based on the predicted outcome for the radiotherapy or the radiotherapy with the particular settings being better than for other therapies or no therapy. In yet another example, the physician selects the therapy based on the predicted outcome and positive results for a cluster-identified similar patient. Other criteria may be used by the physician. The outcome is used to support the decision. The predicted outcome may be used to confirm the choice of the physician.

The machine-learned multi-task generator may have been trained for application for a given clinical problem, such as NSCLC. Since tumors of other clinical problems may have similarities, the same machine-learned multi-task generator may be applied to images and other data for another clinical problem. The generator trained for one organ (e.g., lungs) may be applied for outcome prediction for treatment in another organ (e.g., liver). The same generator may be used for different organs, types of tumors, and/or stages of tumor progression. In alternative embodiments, different generators are trained and applied for different clinical problems. The generator for one clinical problem may be used to initialize the network for training for another clinical problem.

In act 47, the machine-learned multi-task generator is used to refine itself. The initially trained machine-learned multi-task generator or just the initially trained image-to-image network may be applied to the training data. By inputting samples from the training data into the machine-learned generator, outlier samples in the training data may be identified. The pre-trained network is used to identify outliers. Alternatively, the network is to be updated with additional samples. Outliers in the additional samples are identified.

Since the network was trained on handcrafted radiomics or segmentation, the network may be applied on any unknown image with tumor volume to estimate its physical and/or geometrical characteristics. Different from using defined formula, the model was trained on a large number of images so the model would provide more robust estimation of the characteristics. If a large discrepancy between the model output and formula calculation is observed, a potential outlier of the image dataset is identified.

The machine-learned generator or the multi-task generator may be retrained or trained based on the identification of outlier samples. These outliers may be sent for further review or manual corrections. The outliers may be from different types of sources. One simple reason is a large artifact in the region of interest. The artifact may be corrected by applying a threshold to limit the range of image intensity or by filtering. Another possible reason is that some characteristics of the tumor are very different from others in the datasets so the model cannot precisely estimate their values. Applying the defined formula might still return reasonable values, which make this outlier hard to be identified in large datasets. This type of outlier cannot be automatically corrected because the large radiomic discrepancy might suggest important pathology. Manual review of the possible outliers may allow for discarding, inclusion without correction, or correction. Retraining or training then uses the training samples with the outliers corrected or removed.

In act 48, the machine-learned multi-task generator is used to identify the factors (e.g., variables) most prognostic of outcome. Similarly, different machine-learned multi-task generators using different combinations of inputs may be trained. The machine-learned multi-task generator with the combination of inputs providing the greatest accuracy in outcome prediction is selected and applied for patients.

To determine the input data signature, the machine-training architecture is defined to include the appropriate input options. Each type of input data is provided with a separate input layer into the generator. Alternatively, the different inputs are concatenated into one input vector provided to a given input layer. For example, the autoencoder is defined to receive non-image data. The autoencoder may be defined to receive different combinations of image data cropped to tumors, a therapy dose map, image data in which the tumors are less than half a represented region, demographic data, genomic data, and/or clinical data. Different networks and corresponding input options (i.e., type of data) are defined. The training of the different networks results in different machine-trained generators configured to generate an output prediction for therapy. The performance of each trained generator is determined. The machine-learned multi-task generator with the best performance is selected. The selection may consider availability of the type of input data as well.

In one embodiment, prognostic and predictive signatures are found for clinical decision support. Once the machine-learned multi-task generator provides prediction, it is important to identify the most significant prognostic and predictive signatures (biomarkers) from them. An approach like the forward stepwise feature selection in statistical analysis is used. For example, a null model which has no predictors is initialized. Radiomic features extracted from cropped CT images that only includes information of local tumor region (e.g. shape, size and texture of the tumor) are added as an input to the network trained. In a next step, the radiotherapy dose map is added as an input into the model as an additional channel to the computed tomography image, and the network is trained or re-trained. Computed tomography images with larger field of view (e.g. CT of the entire lung) are added as inputs or used to replace the images with the smaller field of view. The larger field of view provides more tumor locality information. The network is trained or retrained. Demographic and/or clinical data may be added into the network, and the network trained or retrained. Other additions and corresponding training or retraining may be used. Various combinations of inputs may be used. The prediction performance is compared before and after adding new variables. The potential prognostic and predictive signatures in terms of input data are identified as resulting in the greatest change in performance from the comparison.

In one embodiment, to quantify the prediction performance, the concordance index (C-index) is measured between a deep reasoner (i.e., the machine-learned multi-task generator) output of survival and the ground truth or actual event time (local survival, LC, progression free survival (PFS) or overall survival OS). The concordance index is a measurement between 0 and 1 that indicates how well the prediction model can order the actual event times: 1 indicates perfect concordance while 0.5 indicates no better concordance than chance. In another embodiment, the Kaplan-Meier survival curves or cumulative incidence curves between high and low failure risk groups are compared. Statistical tests may be used to calculate the significance level of the difference between groups.

Figure 12:
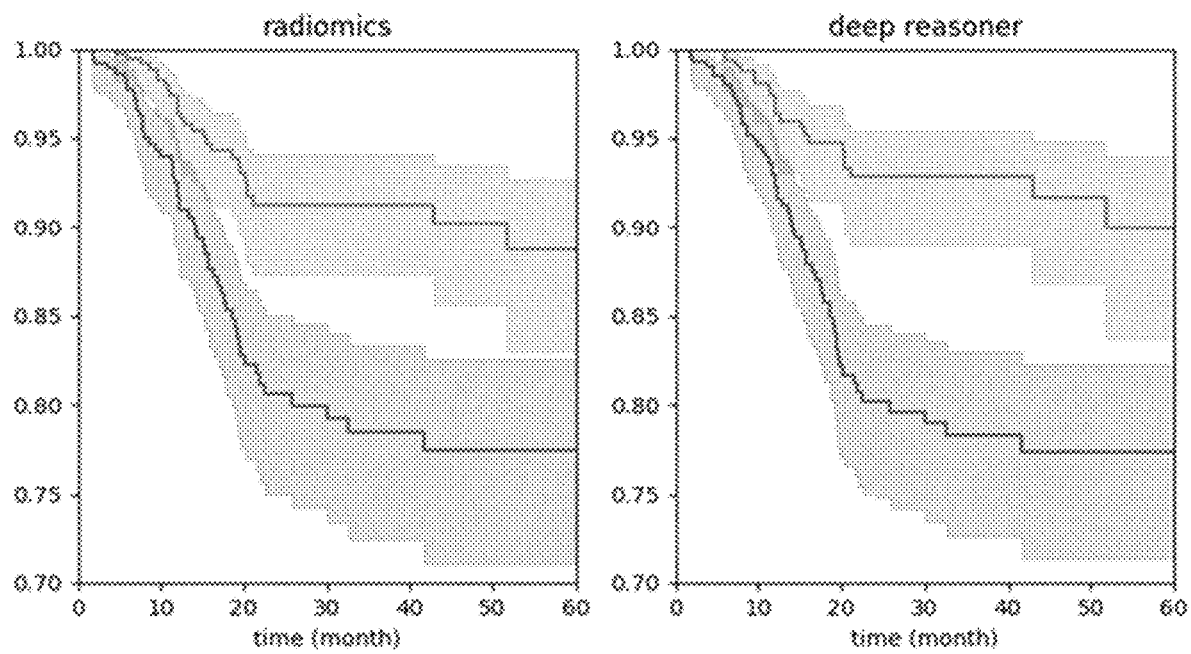
FIG. 12 show a comparison of example outputs of survival using handcrafted radiomics and a multi-task generator.

The performance between (a) using handcrafted radiomics with the quantitative approach of Alerts, et al. "Decoding tumor phenotype by noninvasive imaging using quantitative radiomics approach," Nature Communications, 2014 and (b) a deep reasoner model of FIG. 8 using multi-task training are compared. The concordance index of the deep reasoner method in stratifying patients into two—high and low—therapy failure risk groups is higher in a statistically significant way than that of the radiomics approach. As an example, FIG. 12 shows the local control probability over time for each of the methods. The therapy failure rate reduction of the baseline (no stratification) is compared with that of deep reasoner method and radiomics. A significant reduction within low failure risk groups of both methods results, while the deep reasoner reduction is more significant. Table 1 shows the index and deduction results for both approaches.

TABLE 1

|  | Concordance Index | Log-Rank Tests | 2-yr Failure Rate Deduction |
| --- | --- | --- | --- |
| Radiomics | 0.663 | $x^2_{(1)} = 13.58$ $p < 0.001$ | 31.8% |
| Deep Reasoner | 0.690 | $x^2_{(1)} = 16.18$, $p < 0.0001$ | 44.7% |

The machine-learned multi-task generator or deep reasoner outputs decision support of the clinical workflow in radiotherapy or other therapy. The support is provided based on imaging and/or other non-invasive information, assisting diagnostics and therapy planning with less risk to the patient. With this decision support, clinicians may improve their prediction rate of patient response to therapy based on images. Radiomic features and outcome prediction may help stratify patients that will respond to a certain therapy and redirect the patients that will fail to an alternate therapy regimen.

The machine-learned multi-task generator may be provided with a workstation or medical scanner. In another embodiment, the machine-learned multi-task generator is provided by a server as a service. A physician sends an image to the server, which returns the outcome prediction as a service.

Figure 13:
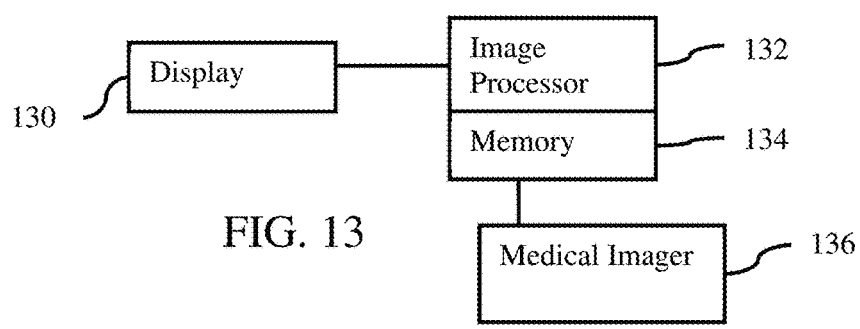
FIG. 13 is a block diagram of one embodiment of a system for therapy decision support.

FIG. 13 shows a medical imaging system for therapy decision support. The system generates a predication of therapy outcome on a display 130 to support therapy decisions.

The medical imaging system includes the display 130, memory 134, and image processor 132. The display 130, image processor 132, and memory 134 may be part of the medical imager 136, a computer, server, workstation, or other system for image processing medical images from a scan of a patient. A workstation or computer without the medical imager 136 may be used as the medical imaging system.

Additional, different, or fewer components may be provided. For example, a computer network is included for remote prediction based on locally captured scan data. As another example, a user input device (e.g., keyboard, buttons, sliders, dials, trackball, mouse, or other device) is provided for user interaction with the outcome prediction.

The medical imager 136 is a computed tomography, magnetic resonance, ultrasound, positron emission tomography, or single photon emission computed tomography scanner. For example, the medical imager 136 is a computed tomography system having an x-ray source and detector connected to a moveable gantry on opposite sides of a patient bed.

The medical imager 136 is configured by settings to scan a patient. The medical imager 136 is setup to perform a scan for the given clinical problem, such as a lung scan. The scan results in scan or image data that may be processed to generate an image of the interior of the patient on the display 103. The scan or image data may represent a three-dimensional distribution of locations (e.g., voxels) in a volume of the patient.

The image processor 132 is a control processor, general processor, digital signal processor, three-dimensional data processor, graphics processing unit, application specific integrated circuit, field programmable gate array, artificial intelligence processor or accelerator, digital circuit, analog circuit, combinations thereof, or other now known or later developed device for processing medical image data. The image processor 132 is a single device, a plurality of devices, or a network. For more than one device, parallel or sequential division of processing may be used. Different devices making up the image processor 132 may perform different functions. In one embodiment, the image processor 132 is a control processor or other processor of a medical diagnostic imaging system, such as the medical imager 136. The image processor 132 operates pursuant to stored instructions, hardware, and/or firmware to perform various acts described herein.

In one embodiment, the image processor 132 is configured to train one or more machine learning networks. Based on a user provided or other source of the network architecture and training data, the image processor 132 learns features for encoders, decoders, discriminators, or other network parts to train the network. A multi-task generator is trained using ground truth and corresponding losses for two or more tasks. One task is outcome prediction. The other task uses data unlabeled for outcome, such as radiomic features, segmentation, non-image data, and/or other information that may be more commonly available than outcome and/or may be derived from the available images.

Alternatively or additionally, the image processor 132 is configured to apply one or more machine-learned generative networks or generators. For example, the image processor 132 applies scan data from the imager 136 to a machine-learned multi-task network. The network predicts a result of therapy for the patient in response to the input of scan data. The network may include an encoder of an autoencoder trained in an unsupervised manner and a fully-connected network configured to receive an output of the encoder to predict the therapy outcome result. The encoder was trained with a decoder of the autoencoder to estimate an input from the output of the encoder in training in the unsupervised manner.

The image processor 132, using the machine-learned network, may predict a time-to-event after therapy for the patient in response to input of scan data. The network may be multi-task as having been trained with a task in addition to the outcome or survival prediction. For example, the training includes loss for segmentation or radiomic or other image features as well as an outcome or survival loss. In application, this extra task may not be used.

The image processor 132 may be configured to cluster. The output of the encoder of the machine-learned network or other deep learned features are used in clustering to identified similar patients. Patients with similar clustering of values of the deep-learned features, such as bottleneck features, are found using the clustering.

The image processor 132 is configured to generate an image. An image showing the predicted outcome is generated. The outcome may be displayed with an image of the interior of the patient, such as a computed tomography image. The predicted result of therapy is displayed for decision support.

The display 130 is a CRT, LCD, projector, plasma, printer, tablet, smart phone or other now known or later developed display device for displaying the output, such as an image with an outcome prediction.

The scan data, training data, network definition, features, machine-learned network, segmentation, radiomic feature values, non-image data, outcome, and/or other information are stored in a non-transitory computer readable memory, such as the memory 134. The memory 134 is an external storage device, RAM, ROM, database, and/or a local memory (e.g., solid state drive or hard drive). The same or different non-transitory computer readable media may be used for the instructions and other data. The memory 134 may be implemented using a database management system (DBMS) and residing on a memory, such as a hard disk, RAM, or removable media. Alternatively, the memory 134 is internal to the processor 132 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 134). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Below are representative aspects in a claiming format. After these representative aspects, the claims of the current application are presented.

A1. A method for decision support in a medical therapy system, the method comprising:
acquiring a medical scan of a patient;
generating a prediction of outcome from therapy for the patient, the outcome generated by a machine-learned multi-task generator having been trained based with both image feature error and outcome error; and
displaying an image of the outcome.

A2. The method of claim 1 wherein acquiring comprises scanning the patient with a computed tomography scanner.

A3. The method of claim 1 wherein acquiring comprises acquiring voxel data representing a three-dimensional distribution of locations in a volume of the patient, and wherein generating comprises generating based on input of the voxel data for a segmented three-dimensional region.

A4. The method of claim 1 wherein generating comprises generating with the machine-learned multi-task generator comprises a convolutional neural network.

A5. The method of claim 1 wherein generating comprises generating with the machine-learned multi-task generator having been trained with deep learning to create features compared to handcrafted radiomics features for the image feature error.

A6. The method of claim 1 wherein generating comprises generating with the machine-learned multi-task generator having been trained with a greater number of training data samples for the image feature error than for the outcome error.

A7. The method of claim 1 wherein generating comprises generating the outcome as a likelihood of therapy failure or tumor recurrence.

A8. The method of claim 1 further comprising identifying one or more outlier samples in training data by the machine-learned multi-task generator, and retraining the machine-learned multi-task generator based on the identification of the outlier samples.

A9. The method of claim 1 wherein generating comprises generating with the machine-learned multi-task generator having been trained with a weighted combination of the image feature error and outcome error as a loss function.

A10. The method of claim 9 wherein generating comprises generating with the machine-learned multi-task generator having been trained with the image feature error comprising a mean square loss function and the outcome error comprising a cross-entropy loss or partial likelihood loss function.

A11. The method of claim 1 wherein generating comprise generating with the machine-learned multi-task generator comprising an encoder for image features and a classifier for the outcome.

A12. The method of claim 1 wherein acquiring and generating are performed for a first clinical problem and further comprising repeating the acquiring and generating for a second clinical problem different than the first clinical problem, the first and second clinical problems being for different organs, the generating for the first and second clinical problems using the same machine-learned multi-task generator.

A13. The method of claim 1 further comprising treating the patient based on the outcome.

A14. A method for machine training decision support in a medical therapy system, the method comprising:
defining a multi-task network with an output layer for outcome estimation and an output layer for image feature estimation;
machine training the multi-task network to estimate image features and to estimate outcome from input medical imaging volumes, the training being based on ground truth outcomes and ground truth image features; and
storing the machine-trained multi-task network.

A15. The method of claim 14 wherein machine training comprises machine training with a loss function comprising a weighted combination of an image feature loss and an outcome loss.

A16. The method of claim 14 wherein machine training comprises training with training data samples for the ground truth outcomes and training data samples for the ground truth image features, the training data samples for the ground truth outcomes being fewer in number than the training data samples for the ground truth image features by an order of magnitude.

A17. The method of claim 14 wherein machine training comprises machine training with outliers removed from or corrected in training data, the outliers identified by a previous iteration of the multi-task network.

A18. A medical imaging system for therapy decision support, the medical imaging system comprising:
a medical imager configured to scan a patient;
an image processor configured to predict a result of therapy for the patient in response to input of scan data from the scan to a multi-task trained network; and
a display configured to display the predicted result.

A19. The medical imaging system of claim 18 wherein the medical imager comprises a computed tomography imager, and wherein the multi-task trained network was trained using a first loss for image features based on handcrafted radiomics and using a second loss for outcome.

A20. The medical imaging system of claim 18 wherein the multi-task trained network comprises a machine-learned encoder for image features and a fully connected network for the prediction of the result of the therapy.

B1. A method for decision support in a medical therapy system, the method comprising:
acquiring a medical scan of a patient;
generating a prediction of survival post therapy for the patient, the survival generated by a machine-learned multi-task generator having been trained based on at least two losses including a survival loss; and
displaying an image of the survival.

B2. The method of claim 1 wherein acquiring comprises scanning the patient with a computed tomography scanner.

B3. The method of claim 1 wherein acquiring comprises acquiring voxel data representing a three-dimensional distribution of locations in a volume of the patient, and wherein generating comprises generating based on input of the voxel data for a segmented three-dimensional region.

B4. The method of claim 1 wherein generating comprises generating with the machine-learned multi-task generator comprises a convolutional neural network.

B5. The method of claim 4 wherein generating comprises generating with the convolutional neural network comprising an encoder network trained as part of an encoder and decoder network, and the convolutional neural network comprising a neural network configured to receive bottleneck features of the encoder network, the neural network generating the survival.

B6. The method of claim 1 wherein the at least two losses include an image feature loss, and wherein generating comprises generating with the machine-learned multi-task generator having been trained with deep learning to create features compared to handcrafted radiomics features for the image feature loss.

B7. The method of claim 1 wherein generating comprises generating with the machine-learned multi-task generator having been trained with a greater number of training data samples for an image feature loss of the at least two losses than for the survival loss.

B8. The method of claim 1 wherein generating comprises generating the survival as a time to event.

B9. The method of claim 1 wherein generating comprises generating with the machine-learned multi-task generator having been trained with the survival loss comprising a maximum likelihood.

B10. The method of claim 1 wherein generating comprises generating with the machine-learned multi-task generator having been trained with deep learning including non-linear relationships between the survival and image features.

B11. The method of claim 1 wherein generating comprises generating the survival as a likelihood as a function of time.

B12. The method of claim 1 further comprising stratifying the survival.

B13. The method of claim 12 further comprising treating the patient based on the stratification.

B14. A method for machine training decision support in a medical therapy system, the method comprising:
    defining a multi-task network with an output layer for survival estimation and an output layer for image feature estimation;
    machine training the multi-task network to estimate image features and to estimate survival from input medical imaging volumes, the training being based on ground truth survivals and ground truth image features; and storing the machine-trained multi-task network.

B15. The method of claim 14 wherein machine training comprises machine training with a loss function comprising a weighted combination of an image feature loss and a survival loss comprising a maximum likelihood.

B16. The method of claim 14 wherein machine training comprises training with training data samples for the ground truth survivals and training data samples for the ground truth image features, the training data samples for the ground truth survivals being fewer in number than the training data samples for the ground truth image features by an order of magnitude.

B17. The method of claim 14 wherein defining comprises defining the multi-task network as an encoder and decoder with a neural network receiving bottleneck features of the encoder and decoder as input, and wherein machine training comprises comparing the ground truth image features compared to an output of the decoder and comparing the ground truth survivals to an output of the neural network.

B18. A medical imaging system for therapy decision support, the medical imaging system comprising:
    a medical imager configured to scan a patient;
    an image processor configured to predict a time-to-event or failure risk after therapy for the patient in response to input of scan data from the scan to a multi-task trained network; and
    a display configured to display the time-to-event or failure risk.

B19. The medical imaging system of claim 18 wherein the medical imager comprises a computed tomography imager, and wherein the multi-task trained network was trained using a first loss for image features based on handcrafted radiomics and using a second loss for the time to event as survival.

B20. The medical imaging system of claim 18 wherein the multi-task trained network comprises a machine-learned encoder for image features and a neural network for the prediction of the time-to-event or failure risk after the therapy.

C1. A method for decision support in a medical therapy system, the method comprising:
    acquiring a medical scan of a patient;
    generating a prediction of outcome of therapy for the patient, the outcome generated by a machine-learned multi-task generator having been trained based on a segmentation loss and an outcome loss; and
    displaying an image of the survival.

C2. The method of claim 1 wherein acquiring comprises scanning the patient with a computed tomography scanner.

C3. The method of claim 1 wherein acquiring comprises acquiring voxel data representing a three-dimensional distribution of locations in a volume of the patient, and wherein generating comprises generating based on input of the voxel data.

C4. The method of claim 1 wherein generating comprises generating with the machine-learned multi-task generator comprises a convolutional neural network.

C5. The method of claim 4 wherein generating comprises generating with the convolutional neural network comprising an encoder network trained as part of an encoder and decoder network, and the convolutional neural network comprising a neural network configured to receive bottleneck features of the encoder network, the neural network generating the outcome.

C6. The method of claim 1 wherein generating comprises generating with the machine-learned multi-task generator having been trained with deep learning to create segmentations compared to ground truth segmentation for the segmentation loss and to compare prediction results to ground truth results for the outcome loss.

C7. The method of claim 1 wherein generating comprises generating with the machine-learned multi-task generator having been trained with a greater number of training data samples for an image feature loss of the at least two losses than for the survival loss.

C8. The method of claim 1 wherein generating comprises generating in response to input of non-image data for the patient to the machine-learned multi-task generator, the machine-learned multi-task generator comprising an autoencoder.

C9. The method of claim 1 wherein generating comprises generating with the machine-learned multi-task generator having been selected from a group of trained networks, each of the trained networks corresponding to different combinations of types of input data.

C10. A method for decision support in a medical therapy system, the method comprising:
    acquiring first non-image data representing characteristics of a patient;
    generating a prediction of outcome of therapy for the patient, the outcome generated by a machine-learned network having been trained as an autoencoder for generating second non-image data representing patients from third non-image data representing other patients, the second non-image data of a same type as the third non-image data; and
displaying an image of the outcome.

C11. The method of claim 10 wherein acquiring the first non-image data comprises acquiring genomic, clinical, measurement, and/or family history data of the patient, and wherein the third non-image data comprise genomic, clinical, measurement, and/or family history data of the other patients.

C12. The method of claim 10 wherein generating comprises generating with the autoencoder comprising an encoder network trained as part of an encoder and decoder network, and a fully connected network configured to receive bottleneck features of the encoder network, the fully connected network generating the outcome.

C13. The method of claim 1 wherein generating comprises generating with the machine-learned network having been trained with multi-task deep learning to create segmentations compared to ground truth segmentation for a segmentation loss and to create outcome predictions compared to ground truth results for an outcome loss.

C14. The method of claim 1 wherein generating comprises generating with the machine-learned network having been selected from a group of trained networks, each of the trained networks corresponding to different combinations of types of input data.

C15. A method for machine training decision support in a medical therapy system, the method comprising:
defining a machine-training architecture with a plurality of data input options, each data input option corresponding to a different type of data;
machine training the machine-training architecture with different combinations of one or more of the data input options, the machine training with the different combinations resulting in different machine-trained generators configured to generate an output prediction for therapy;
determining performance of each of the machine-trained generators;
selecting one of the machine-trained generators based on the performance; and
storing the selected machine-trained generator.

C16. The method of claim 15 wherein machine training comprises machine training as a multi-task operation with a loss function comprising a weighted combination of an image feature loss and an outcome loss.

C17. The method of claim 15 wherein defining comprises defining the machine-training architecture as an autoencoder where the data input options comprise non-image data and as a neural network configured to receive bottleneck features from the autoencoder, the neural network trained to generate the prediction.

C18. The method of claim 15 wherein defining comprises defining with the different types of data comprising image data cropped to tumors, a therapy dose map, image data in which the tumors are less than half a represented region, demographic data, and clinical data.

D1. A method for decision support in a medical therapy system, the method comprising:
acquiring a medical scan of a patient;
generating a prediction of outcome of therapy for the patient from scan data of the medical scan, the outcome generated by a machine-learned multi-task generator having been trained with unsupervised learning from training data unlabeled for the outcome and having been trained from labeled training data for the outcome; and
displaying an image of the outcome.

D2. The method of claim 1 wherein acquiring comprises scanning the patient with a computed tomography scanner.

D3. The method of claim 1 wherein acquiring comprises acquiring voxel data representing a three-dimensional distribution of locations in a volume of the patient, and wherein generating comprises generating based on input of the voxel data.

D4. The method of claim 1 wherein generating comprises generating with the machine-learned multi-task generator comprises an autoencoder having been trained with the unsupervised learning.

D5. The method of claim 4 wherein generating comprises generating with the training data unlabeled for the outcome comprising tumor segmentation, non-image data, and/or radiomic image features.

D6. The method of claim 4 wherein generating comprises generating with the machine-learned multi-task generator comprising a fully-connected network configured to receive input from a bottleneck of the autoencoder, the fully-connected network having been trained from the labeled training data.

D7. The method of claim 6 wherein generating comprises generating in response to input of a scale and intensity normalized version of the scan data and in response to input of a scale, intensity maximum, and intensity minimum for the version of the medical scan.

D8. The method of claim 4 wherein generating comprises generating with the autoencoder comprising an encoder network trained as part of an encoder and decoder network and with the machine-learned multi-task generator comprising a neural network configured to receive bottleneck features of the encoder network, the neural network generating the outcome.

D9. The method of claim 1 further comprising applying therapy to the patient based on the outcome.

D10. The method of claim 1 further comprising clustering image features from a bottleneck of an encoder of the machine-learned multi-task generator and identifying another patient based on the clustering.

D11. A medical imaging system for therapy decision support, the medical imaging system comprising:
a medical imager configured to scan a patient;
an image processor configured to predict a result of therapy for the patient in response to input of scan data from the scan to a machine-trained network, the machine-trained network including an encoder of an autoencoder trained in an unsupervised manner and a fully-connected network configured to receive an output of the encoder to predict the result; and
a display configured to display the predicted result.

D12. The medical imaging system of claim 11 wherein the medical imager comprises a computed tomography imager, and wherein the machine-trained network was trained using a first loss for image features or segmentation and using a second loss for outcome.

D13. The medical imaging system of claim 11 wherein the machine-trained network comprises the encoder where the autoencoder comprised the encoder and a decoder to estimate an input from the output of the encoder in the training in the unsupervised manner.

D14. The medical imaging system of claim 11 wherein the fully-connected network comprises a fully-connected multi-layer perceptron.

D15. The medical imaging system of claim 11 wherein the image processor is configured to cluster the output of the encoder and identify another patient based on the cluster of the output of the encoder.

D16. A method for decision support in a medical therapy system, the method comprising:
acquiring a medical scan of a patient;
generating values for bottleneck features of a machine-learned autoencoder having been trained with unsupervised learning from training data unlabeled for a therapy outcome;
clustering the values for the bottleneck features;
identifying another patient based on the values as clustered; and
displaying therapy data for the other patient.

D17. The method of claim 16 wherein acquiring comprises scanning the patient with a computed tomography scanner.

D18. The method of claim 16 wherein generating further comprises generating with the machine-learned autoencoder comprising a multi-task generator configured to generate an output of therapy for the patient from the values for the bottleneck features.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for decision support in a medical therapy system, the method comprising:
   acquiring a medical scan of a patient;
   generating a prediction of outcome from therapy for the patient, the outcome generated by a machine-learned multi-task generator having been trained based with both image feature error and outcome error; and
   displaying an image of the outcome.

2. The method of claim 1 wherein acquiring comprises scanning the patient with a computed tomography scanner.

3. The method of claim 1 wherein acquiring comprises acquiring voxel data representing a three-dimensional distribution of locations in a volume of the patient, and wherein generating comprises generating based on input of the voxel data for a segmented three-dimensional region.

4. The method of claim 1 wherein generating comprises generating with the machine-learned multi-task generator comprises a convolutional neural network.

5. The method of claim 1 wherein generating comprises generating with the machine-learned multi-task generator having been trained with deep learning to create features compared to handcrafted radiomics features for the image feature error.

6. The method of claim 1 wherein generating comprises generating with the machine-learned multi-task generator having been trained with a greater number of training data samples for the image feature error than for the outcome error.

7. The method of claim 1 wherein generating comprises generating the outcome as a likelihood of therapy failure or tumor recurrence.

8. The method of claim 1 further comprising identifying one or more outlier samples in training data by the machine-learned multi-task generator, and retraining the machine-learned multi-task generator based on the identification of the outlier samples.

9. The method of claim 1 wherein generating comprises generating with the machine-learned multi-task generator having been trained with a weighted combination of the image feature error and outcome error as a loss function.

10. The method of claim 9 wherein generating comprises generating with the machine-learned multi-task generator having been trained with the image feature error comprising a mean square loss function and the outcome error comprising a cross-entropy loss or partial likelihood loss function.

11. The method of claim 1 wherein generating comprise generating with the machine-learned multi-task generator comprising an encoder for image features and a classifier for the outcome.

12. The method of claim 1 wherein acquiring and generating are performed for a first clinical problem and further comprising repeating the acquiring and generating for a second clinical problem different than the first clinical problem, the first and second clinical problems being for different organs, the generating for the first and second clinical problems using the same machine-learned multi-task generator.

13. The method of claim 1 further comprising treating the patient based on the outcome.

14. A method for machine training decision support in a medical therapy system, the method comprising:
   defining a multi-task network with an output layer for outcome estimation and an output layer for image feature estimation;
   machine training the multi-task network to estimate image features and to estimate outcome from input medical imaging volumes, the training being based on ground truth outcomes and ground truth image features; and
   storing the machine-trained multi-task network.

15. The method of claim 14 wherein machine training comprises machine training with a loss function comprising a weighted combination of an image feature loss and an outcome loss.

16. The method of claim 14 wherein machine training comprises training with training data samples for the ground truth outcomes and training data samples for the ground truth image features, the training data samples for the ground truth outcomes being fewer in number than the training data samples for the ground truth image features by an order of magnitude.

17. The method of claim 14 wherein machine training comprises machine training with outliers removed from or corrected in training data, the outliers identified by a previous iteration of the multi-task network.

18. A medical imaging system for therapy decision support, the medical imaging system comprising:
   a medical imager configured to scan a patient;
   an image processor configured to predict a result of therapy for the patient in response to input of scan data from the scan to a multi-task trained network; and
   a display configured to display the predicted result.

19. The medical imaging system of claim 18 wherein the medical imager comprises a computed tomography imager, and wherein the multi-task trained network was trained using a first loss for image features based on handcrafted radiomics and using a second loss for outcome.

20. The medical imaging system of claim 18 wherein the multi-task trained network comprises a machine-learned encoder for image features and a fully connected network for the prediction of the result of the therapy.

* * * * *